(12) United States Patent
Bell et al.

(10) Patent No.: US 6,194,207 B1
(45) Date of Patent: Feb. 27, 2001

(54) METHODS FOR THE SELECTIVE EXPANSION OF LYMPHOCYTES BY IN VITRO CULTIVATION

(75) Inventors: David N. Bell, Oakville; Truman Wong, North York, both of (CA)

(73) Assignee: Hemosol Inc., Etobicoke (CA)

( * ) Notice: Subject to any disclaimer, the term of this patent is extended or adjusted under 35 U.S.C. 154(b) by 0 days.

(21) Appl. No.: 09/016,784

(22) Filed: Jan. 30, 1998

Related U.S. Application Data

(60) Provisional application No. 60/037,245, filed on Jan. 31, 1997.

(51) Int. Cl.[7] .............................. A01N 1/02; A01N 63/00; C12N 5/02; C12N 5/08
(52) U.S. Cl. ............................ 435/377; 435/2; 424/93.71
(58) Field of Search ..................... 435/2, 377; 424/93.71

(56) References Cited

U.S. PATENT DOCUMENTS 4,490,289 * 12/1984 Stern ..................................... 530/351

OTHER PUBLICATIONS

Tice, D.G. and Davey, F.R. Separation of human T–lymphocyte colony–forming cells on percoll gradients. Prep. Blochem. 13(5):461–474, 1983.*

* cited by examiner

*Primary Examiner*—David Saunders
*Assistant Examiner*—Mary Beth Tung
(74) *Attorney, Agent, or Firm*—Bereskin & Parr; Micheline Gravelle

(57) ABSTRACT

The invention is directed to methods for the production of selected populations of lymphocytes. Lymphocytes produced can be isolated and purified using well known and established procedures to provide a consistent lymphocyte source which one of ordinary skill in the art can modify to provide an appropriate type or an optimal level of a desired lymphocyte. The availability of such cell populations allows for not only for the complete reconstitution of the depleted, defective or missing lymphocyte population in a patient, but also provides the flexibility of having sufficient cells to permit multiple or cyclic treatments. These methods for expanding target cell populations are broadly applicable to the selective expansion of several types of lymphocytes and are demonstrated to maintain phenotype as well as antigen specificity.

6 Claims, 30 Drawing Sheets

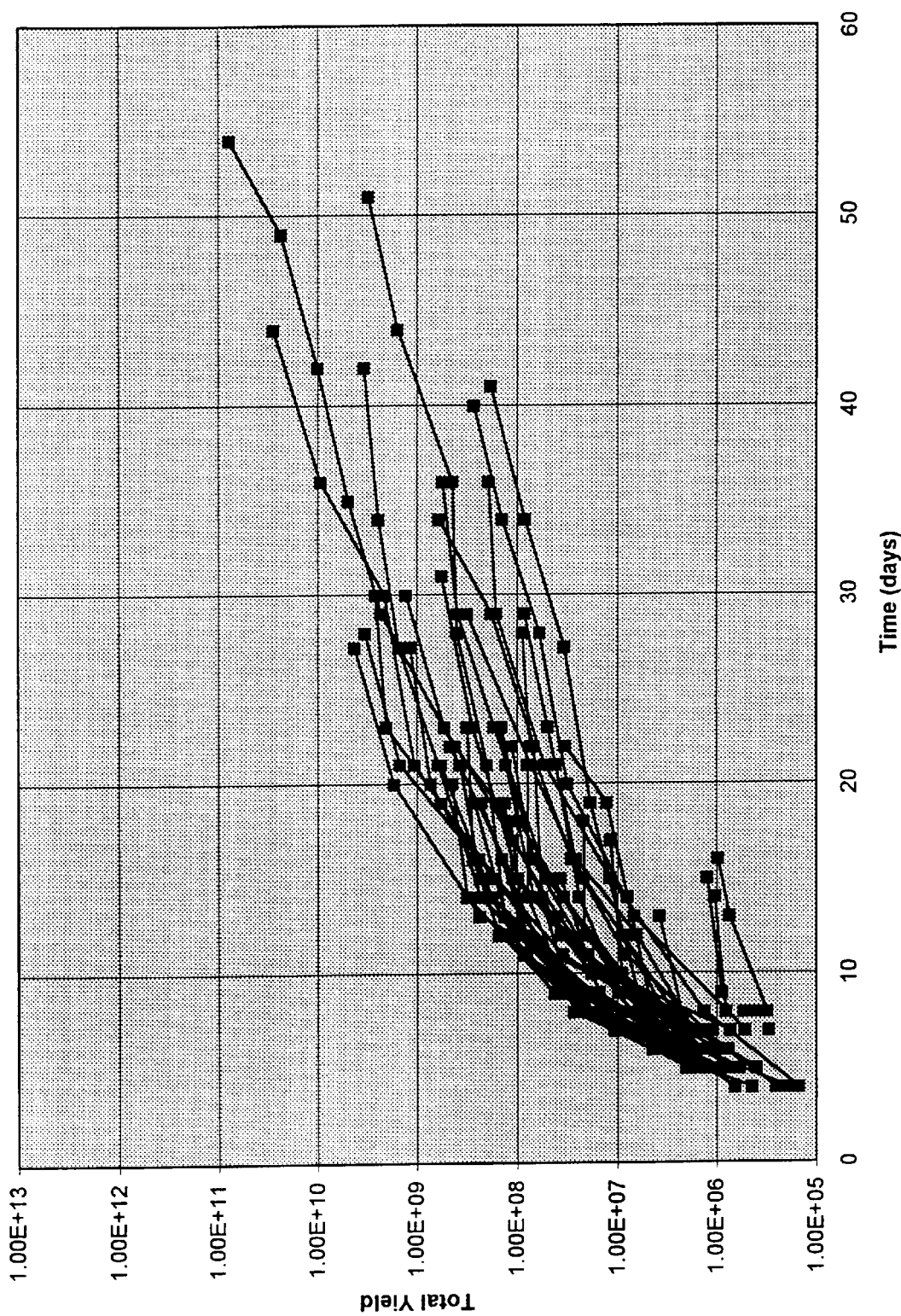
Figure 1a: Cumulative Cell Yield (Cord Blood - CM)

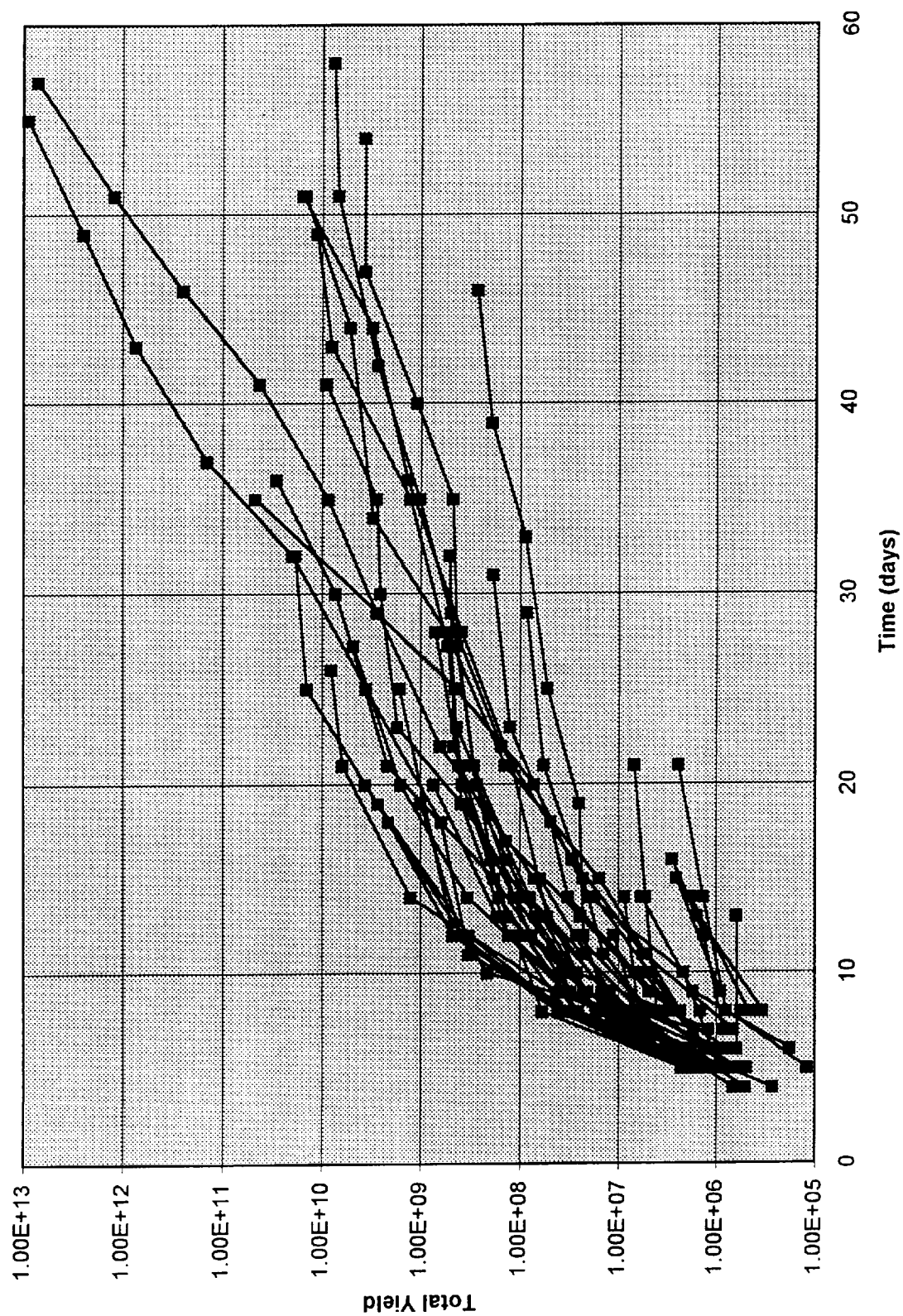

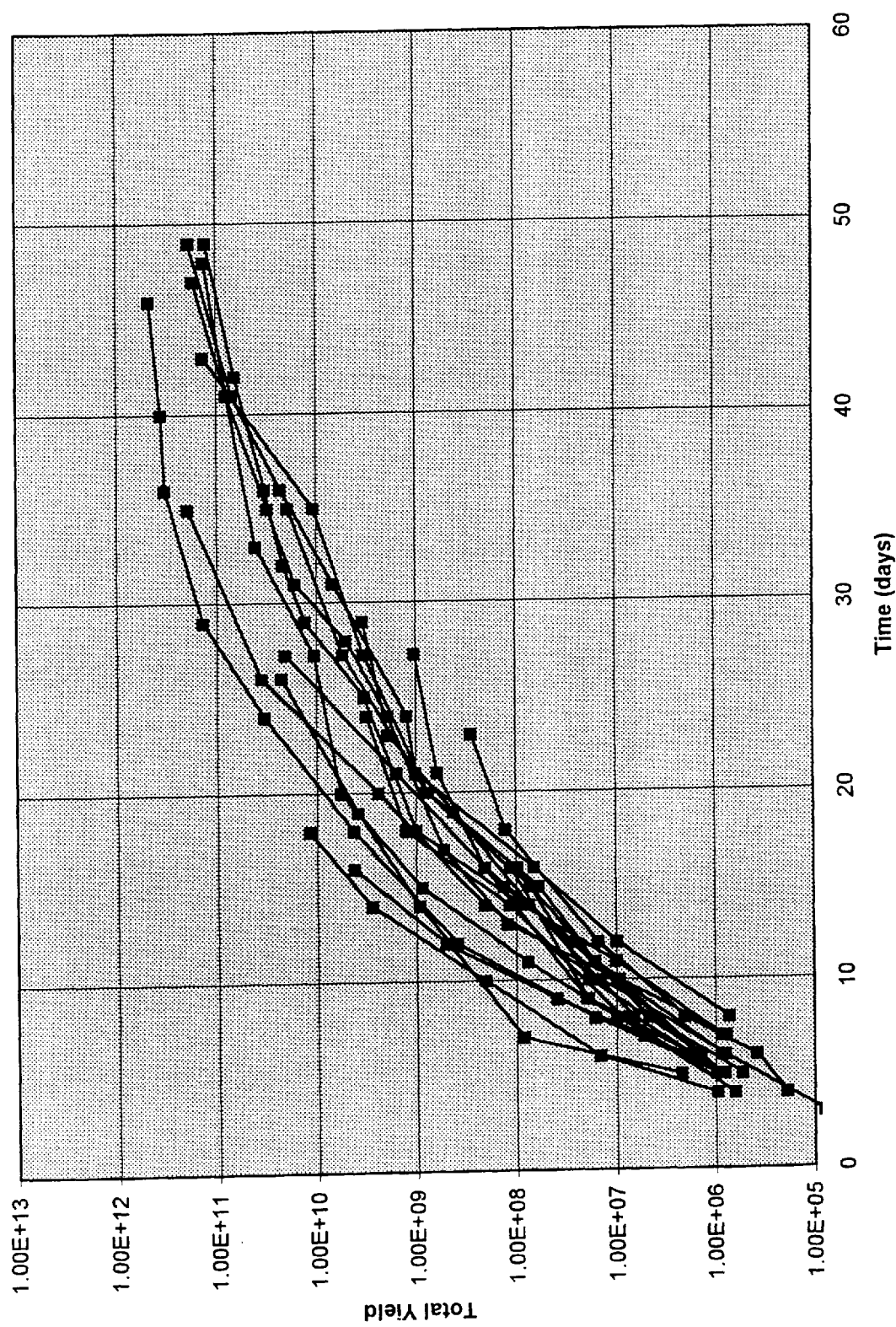

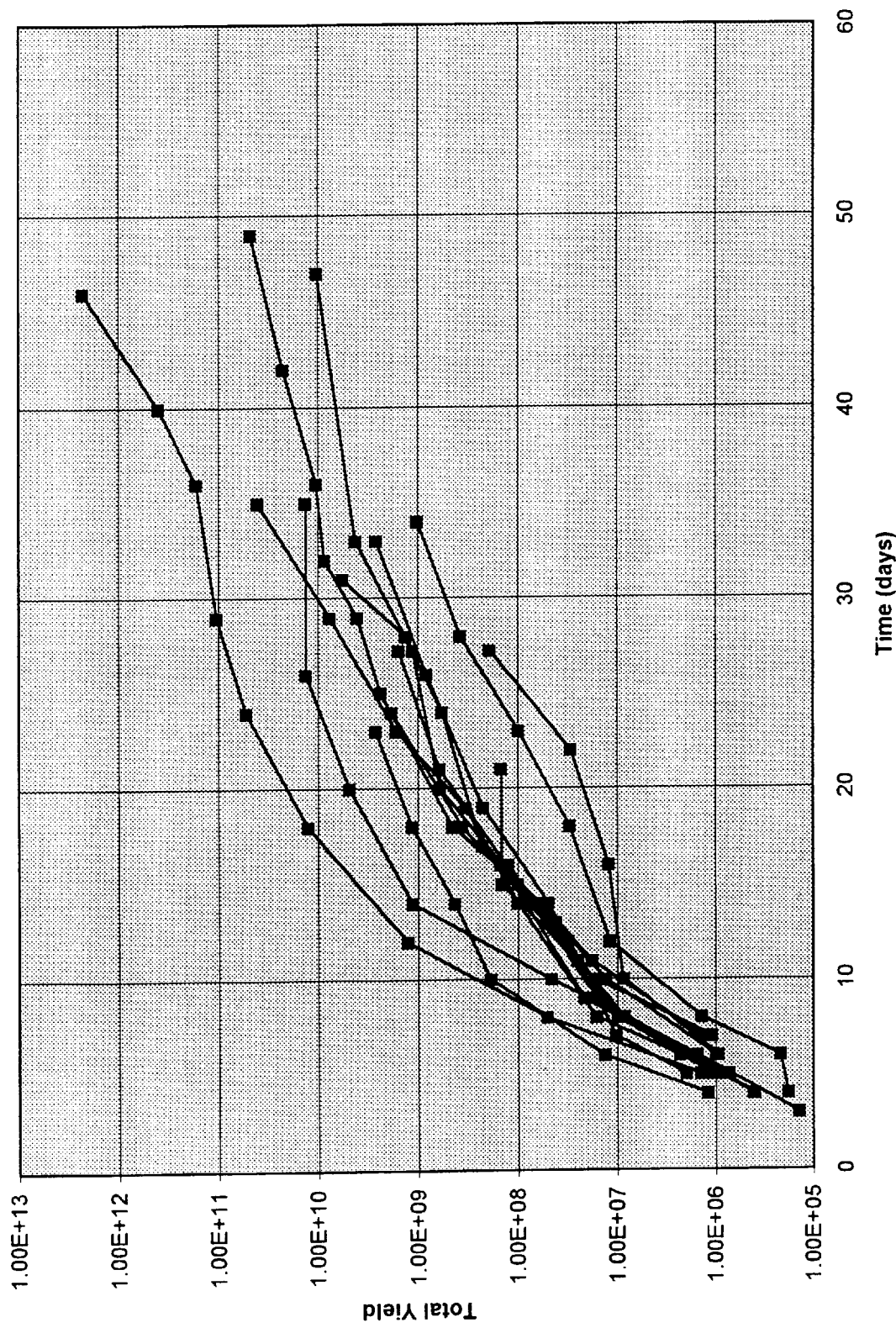

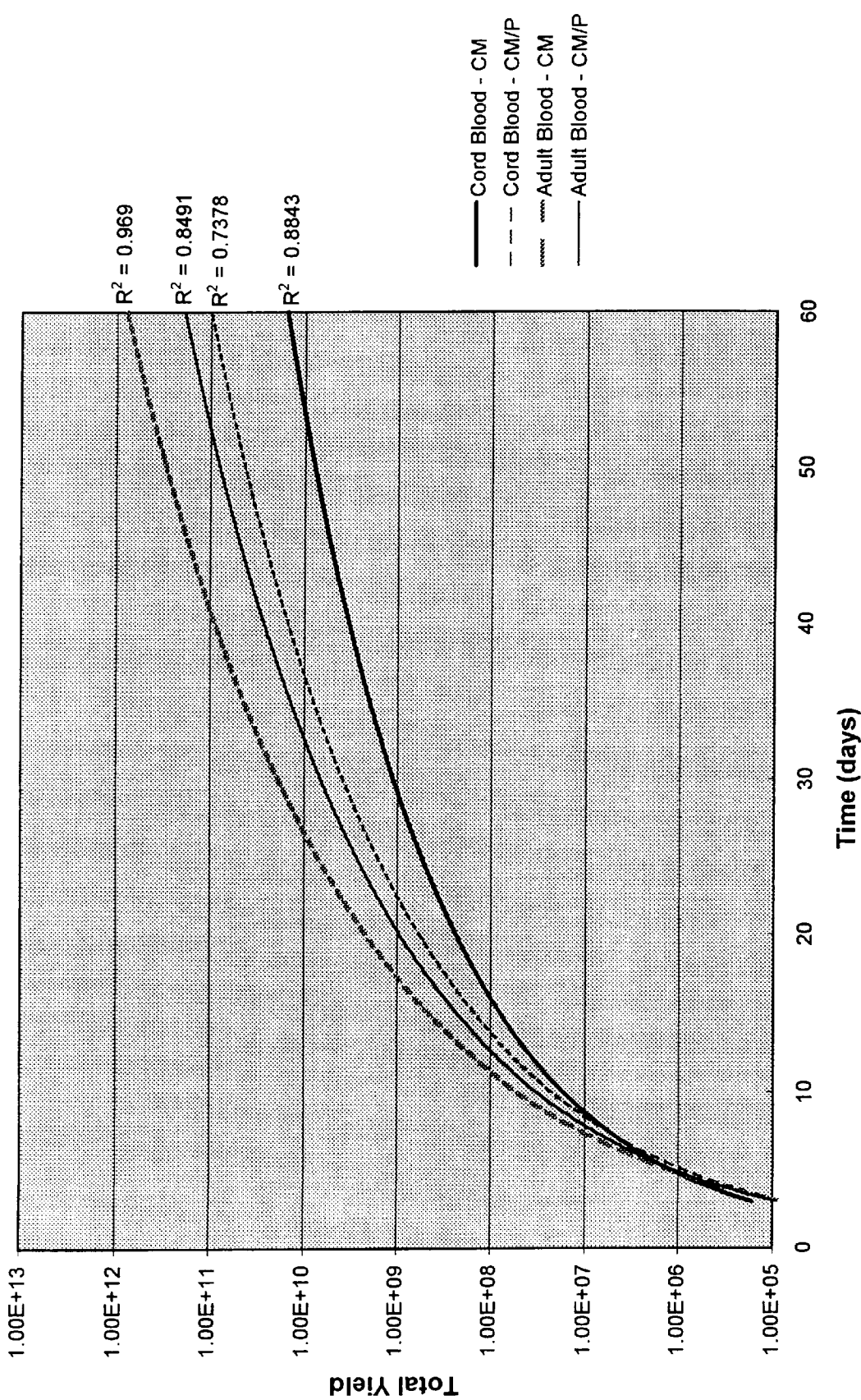

* cultures expired

* cultures expired

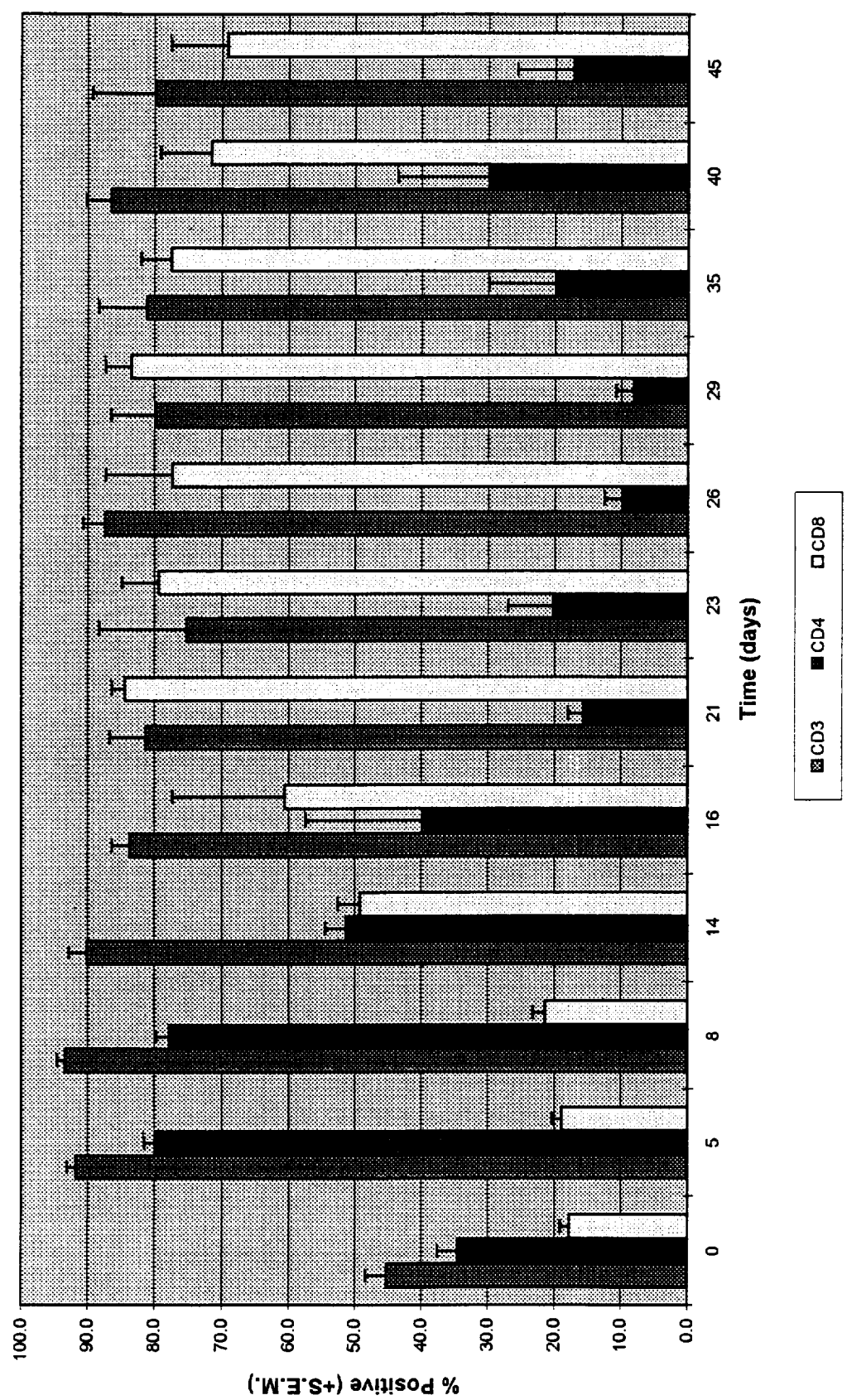

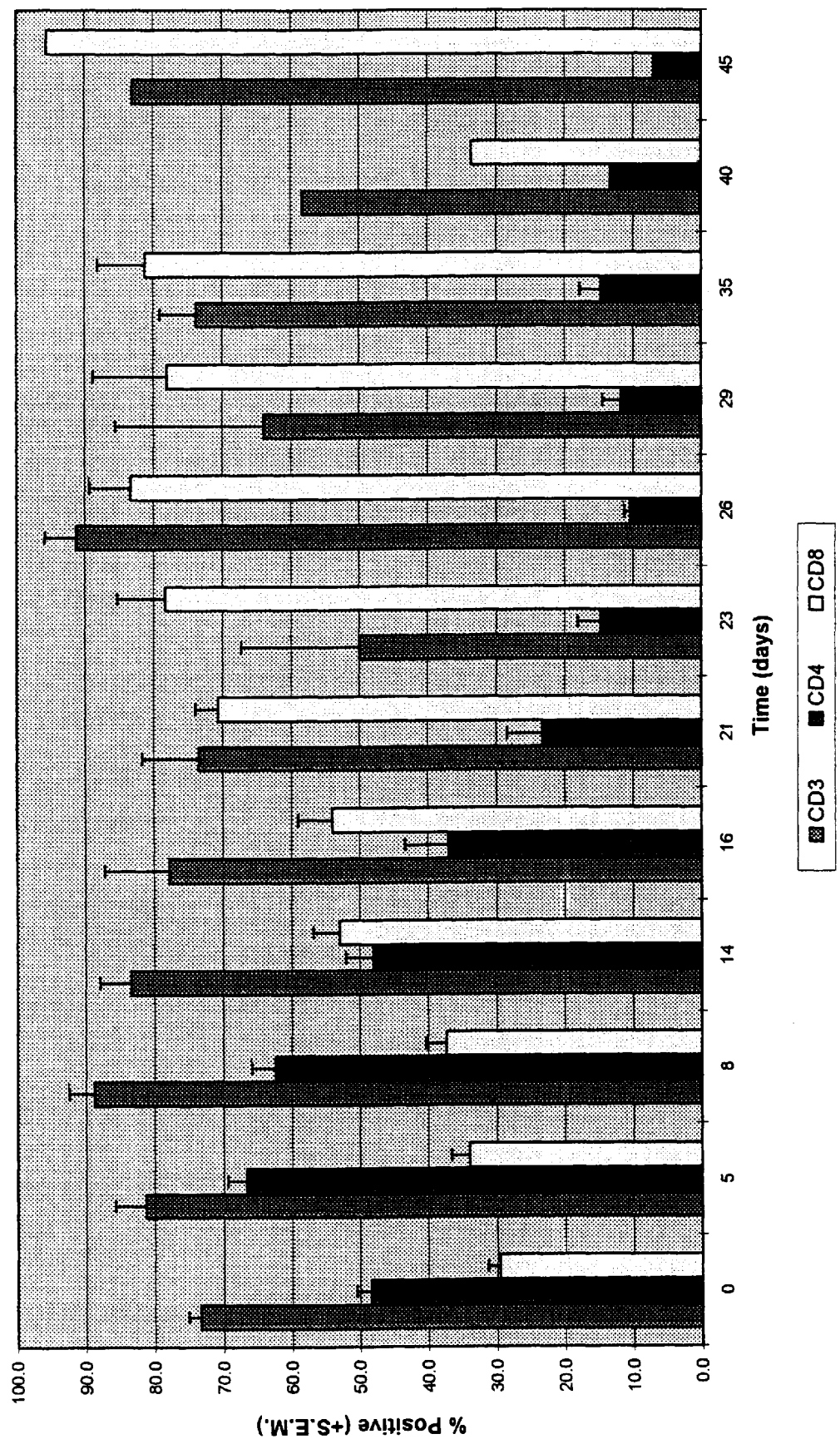
Figure 5: Average per cent of CD3+, CD4+, and CD8+ Adult Blood Cells during Culture with CM

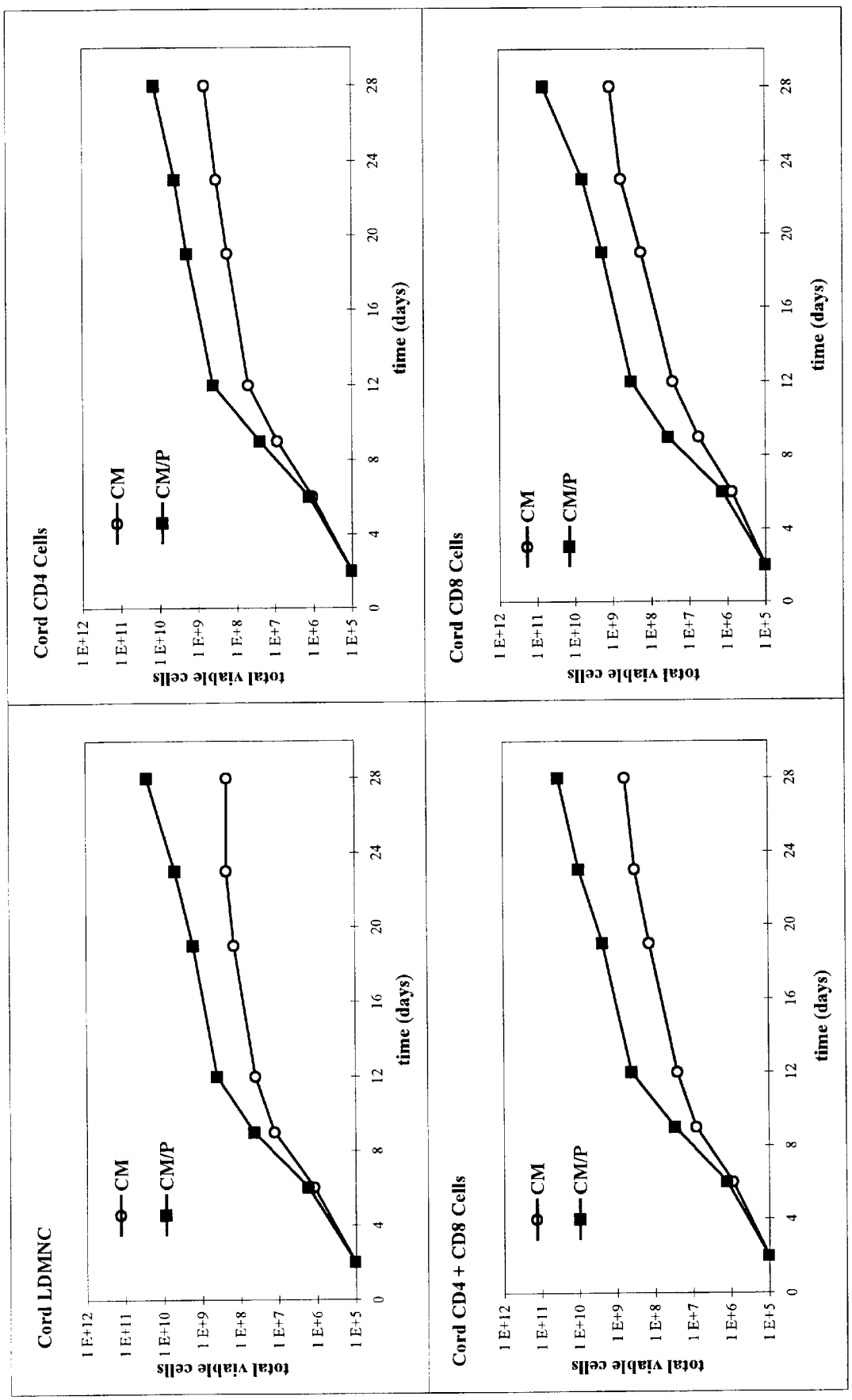
Figure 6: Expansion of Umbilical Cord Blood T Cell Subsets with CM and CM/P Figure 7a
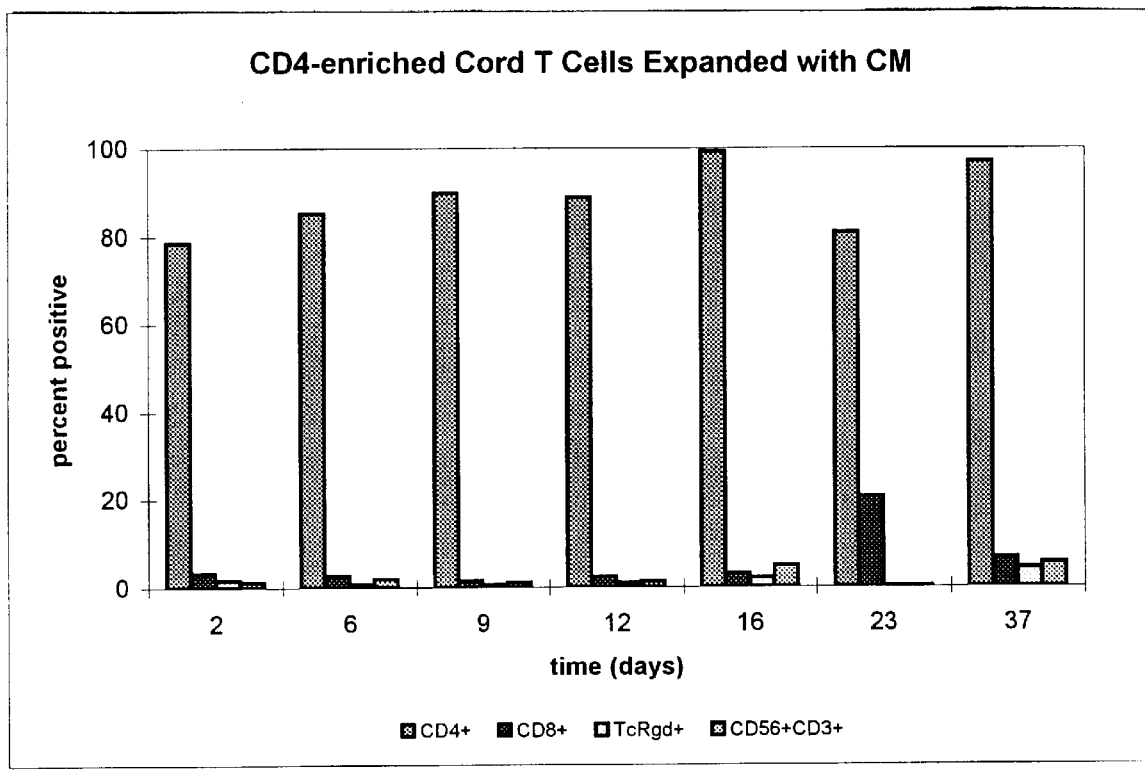
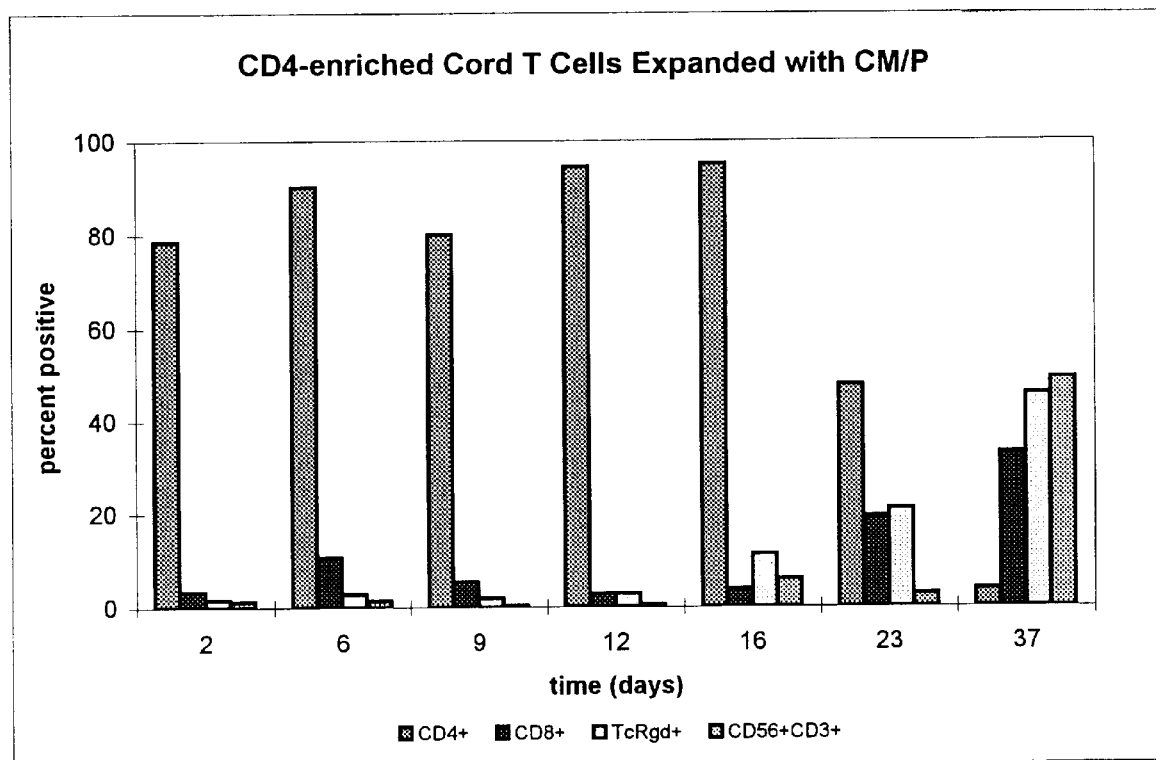

Figure 7b
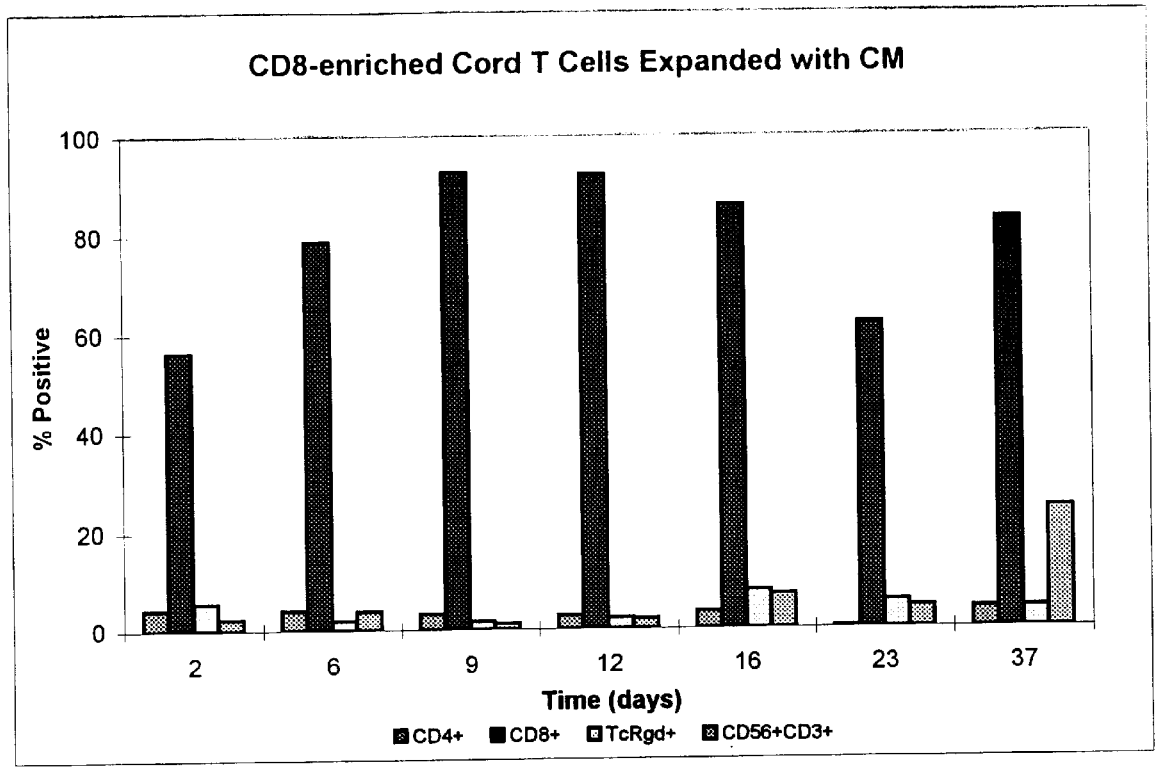
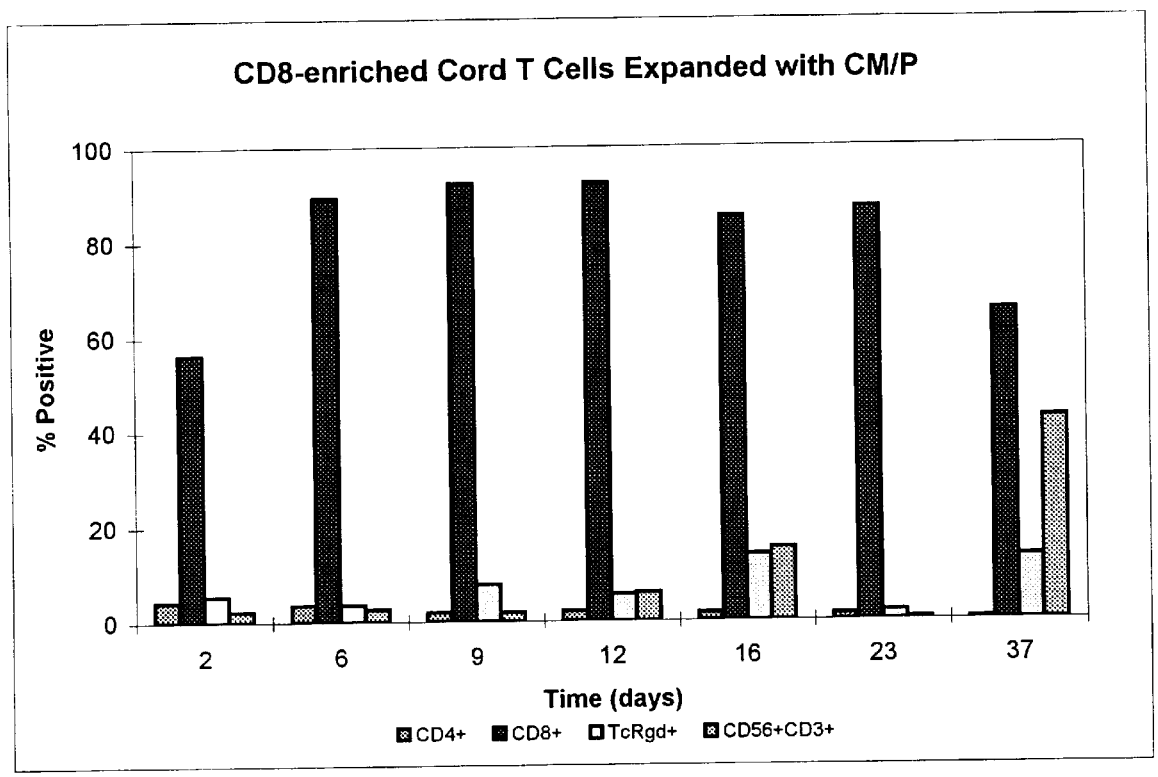

Figure 7c
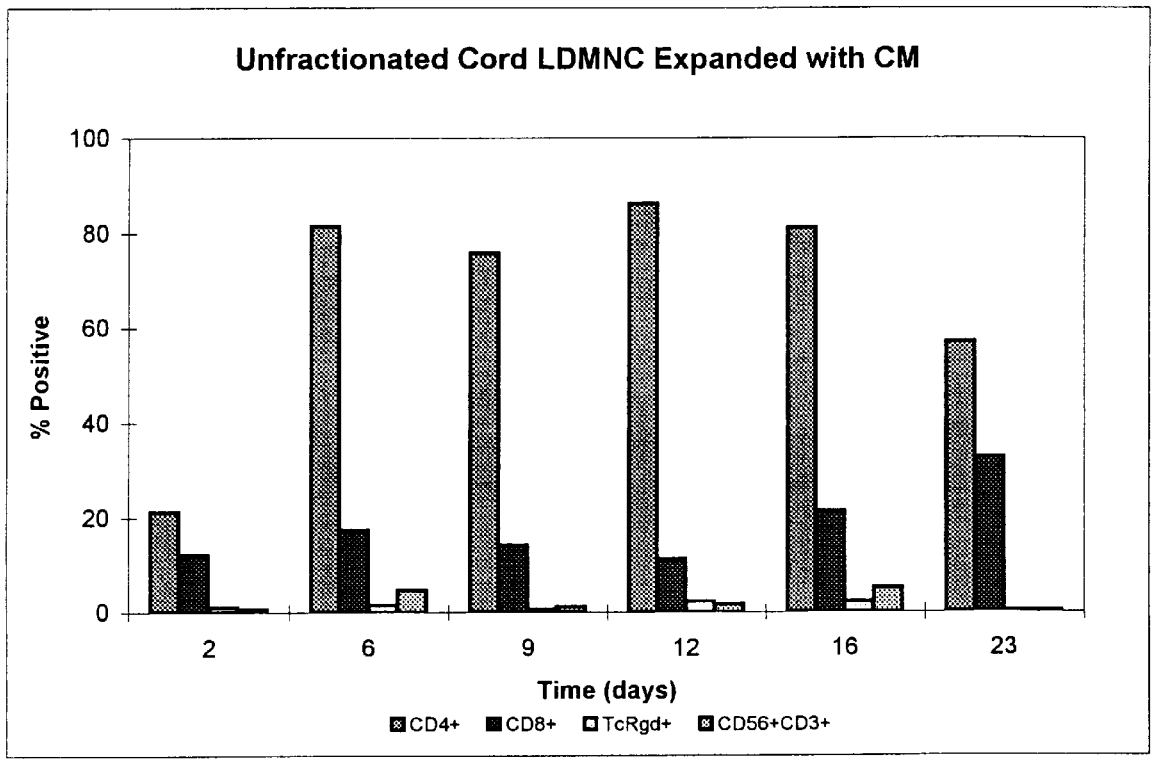
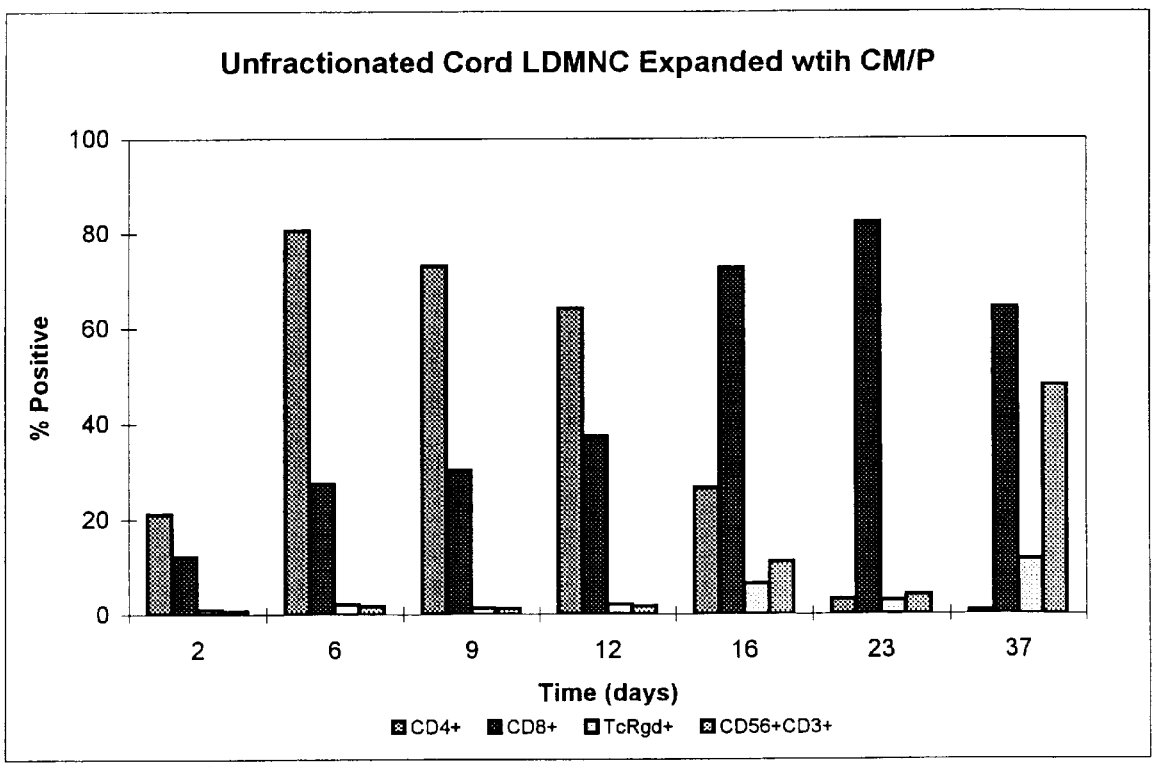

Figure 7d
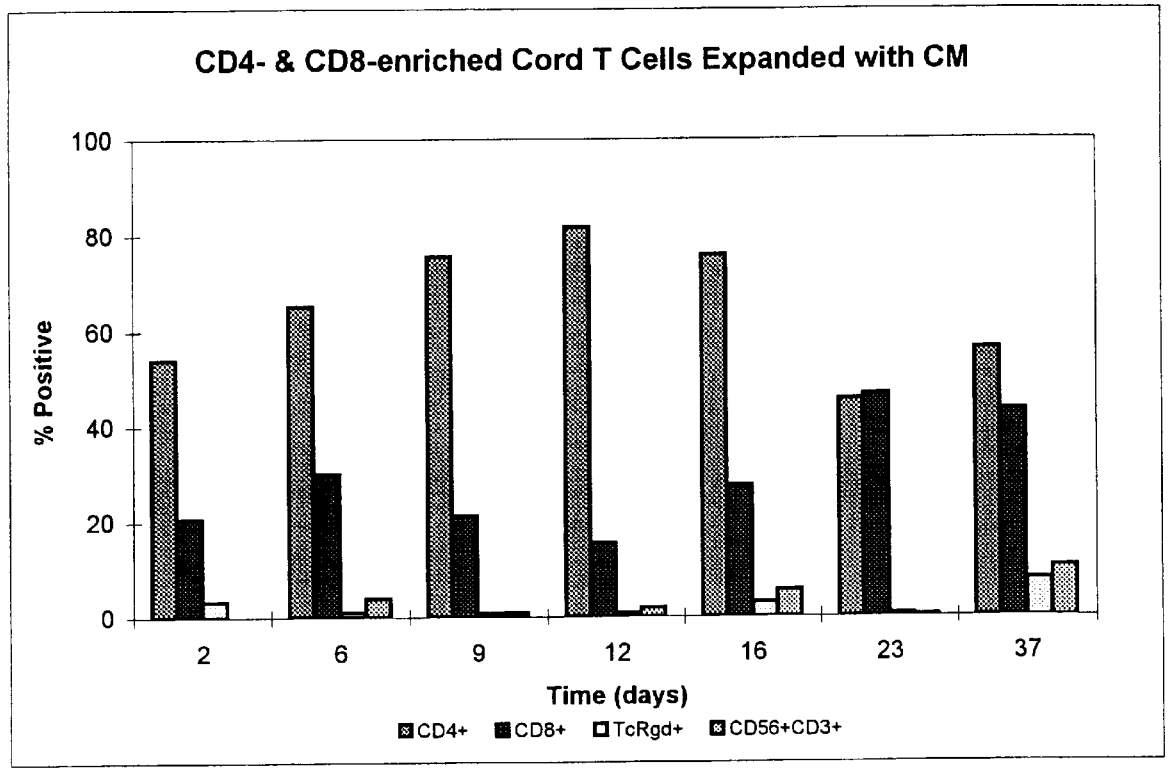
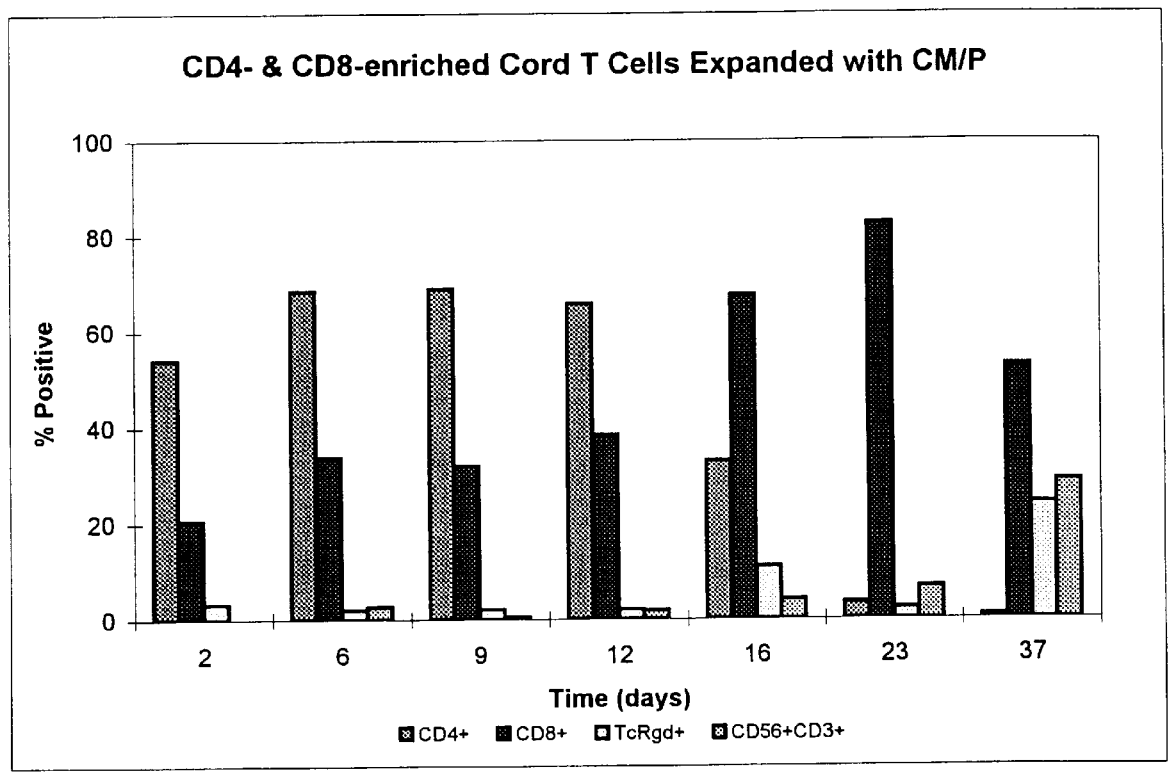

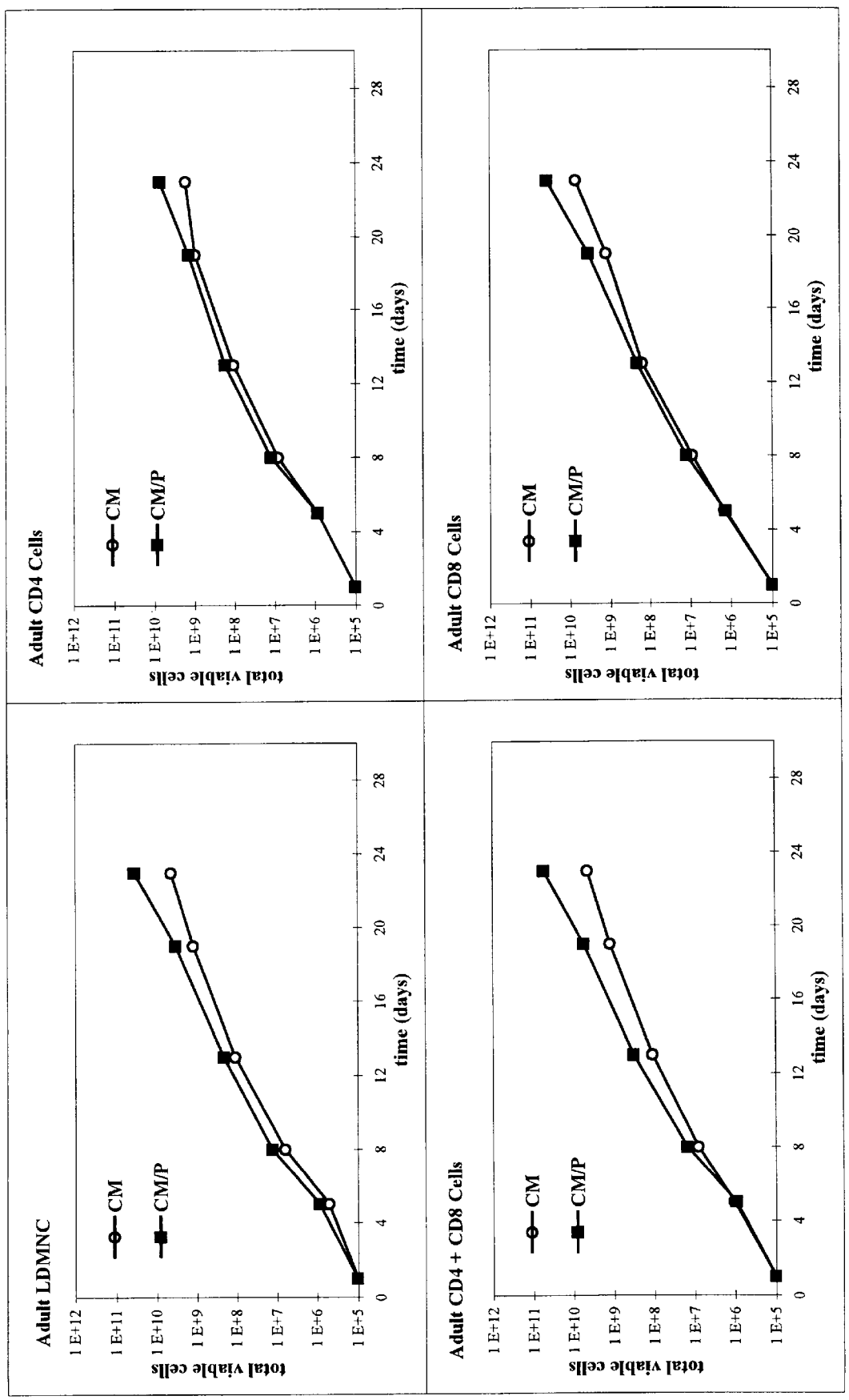
Figure 8: Expansion of Adult Peripheral Blood T Cell Subsets with CM and CM/P Figure 9a
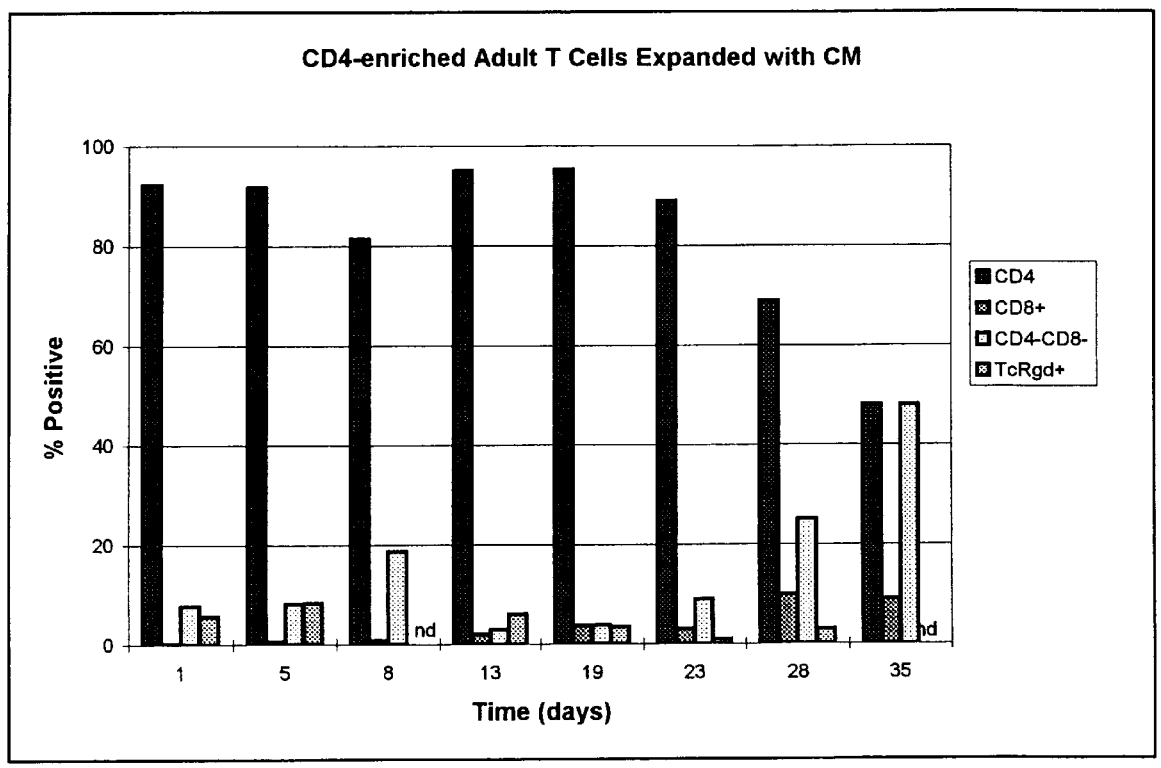
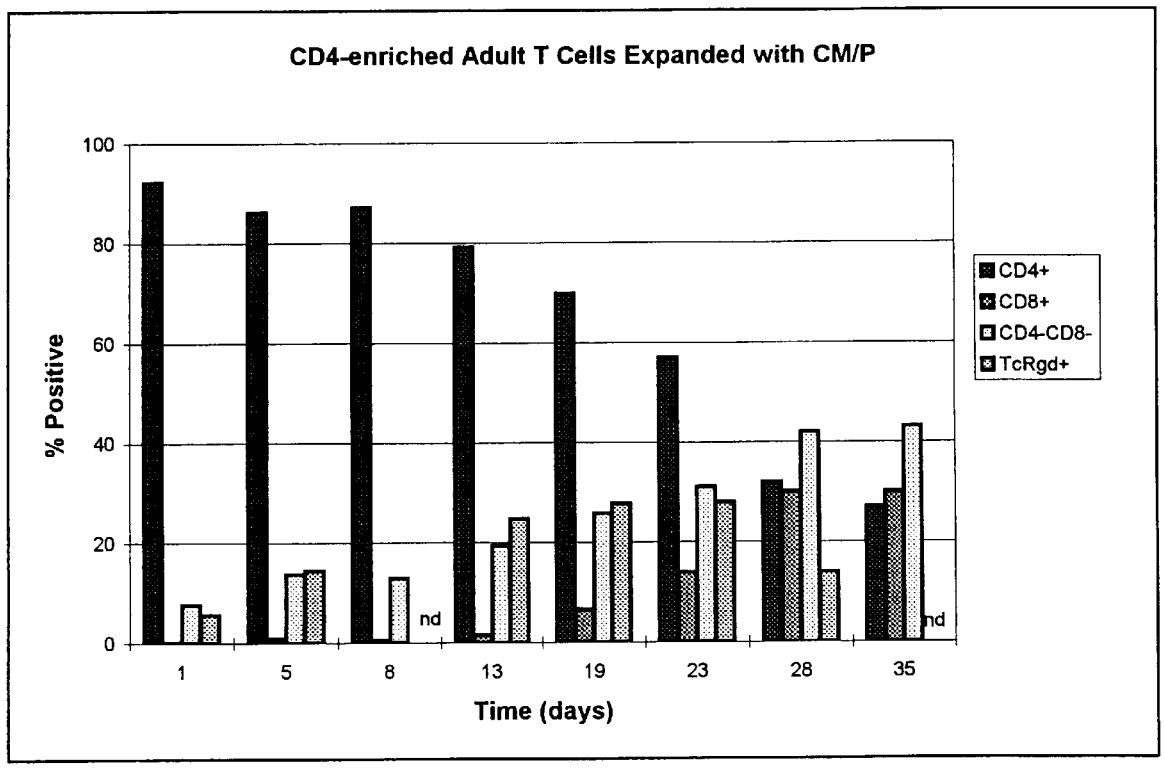

Figure 9b
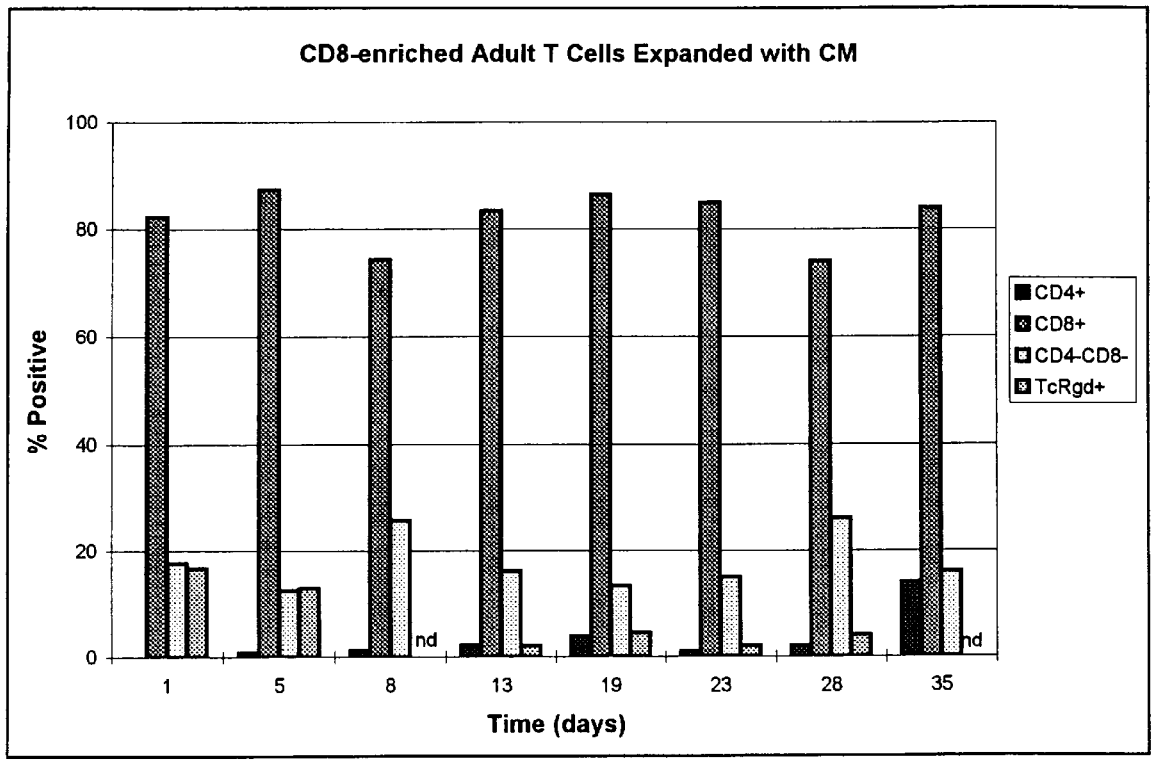
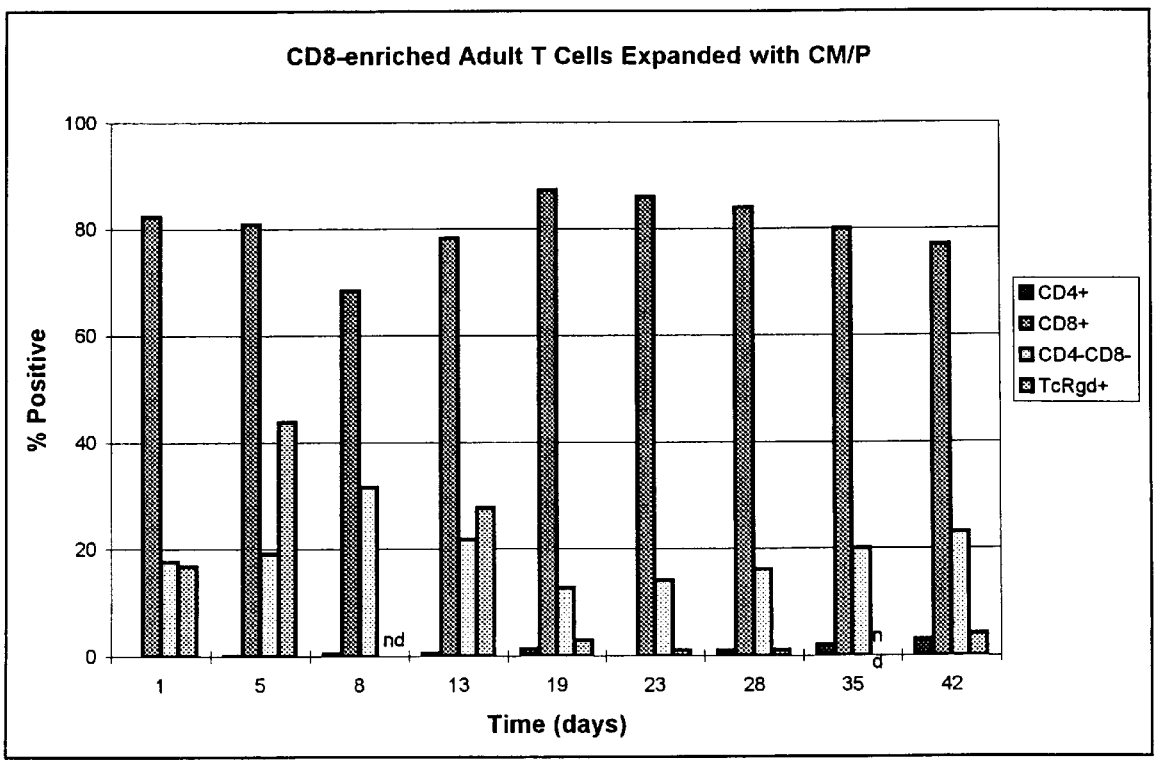

Figure 9c
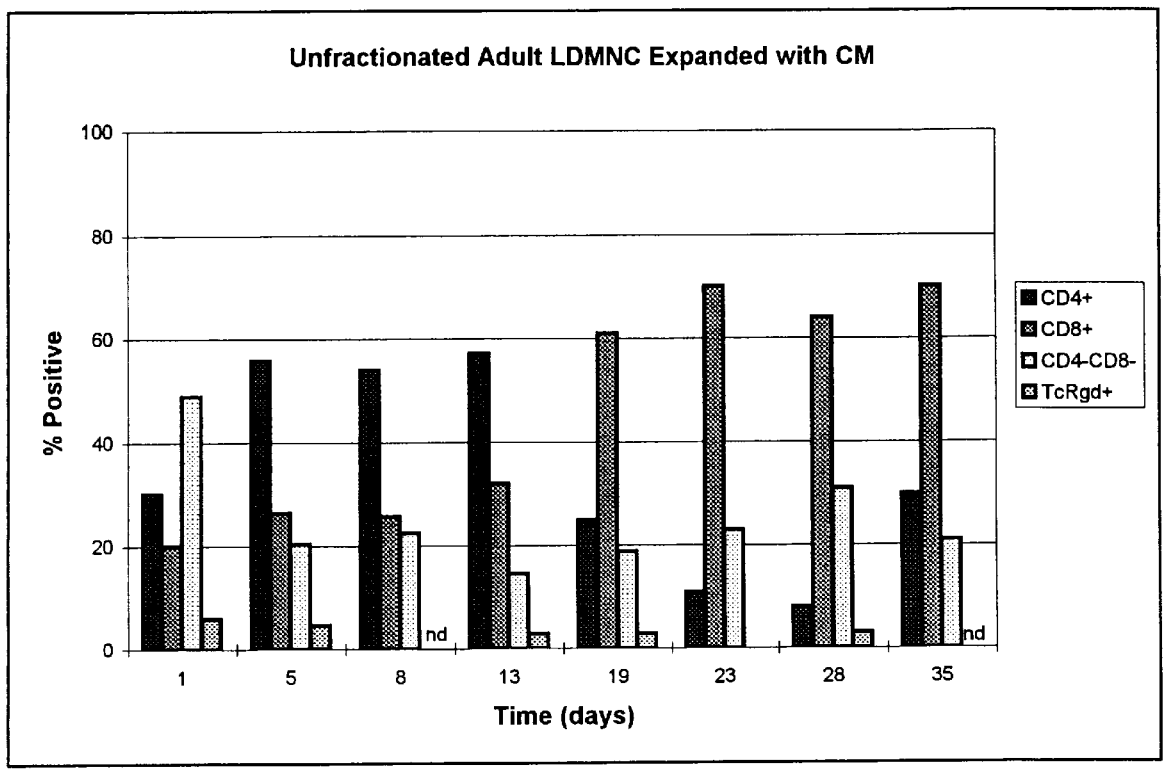
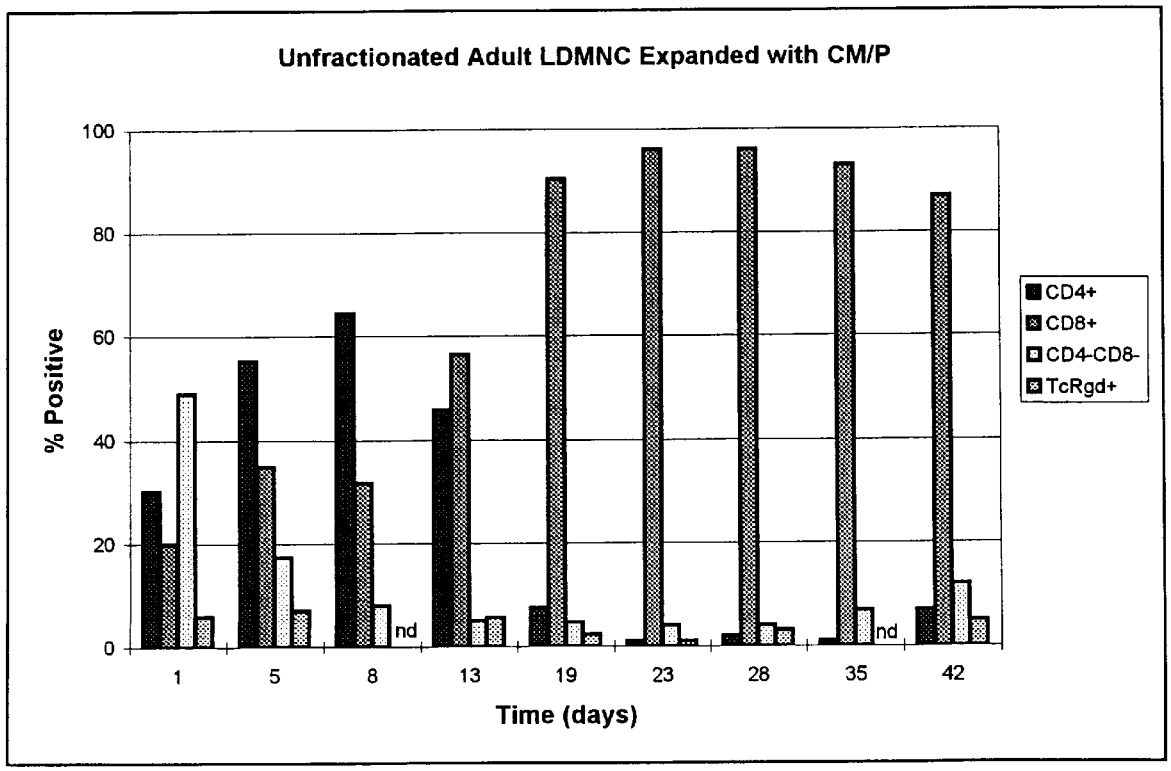

Figure 9d
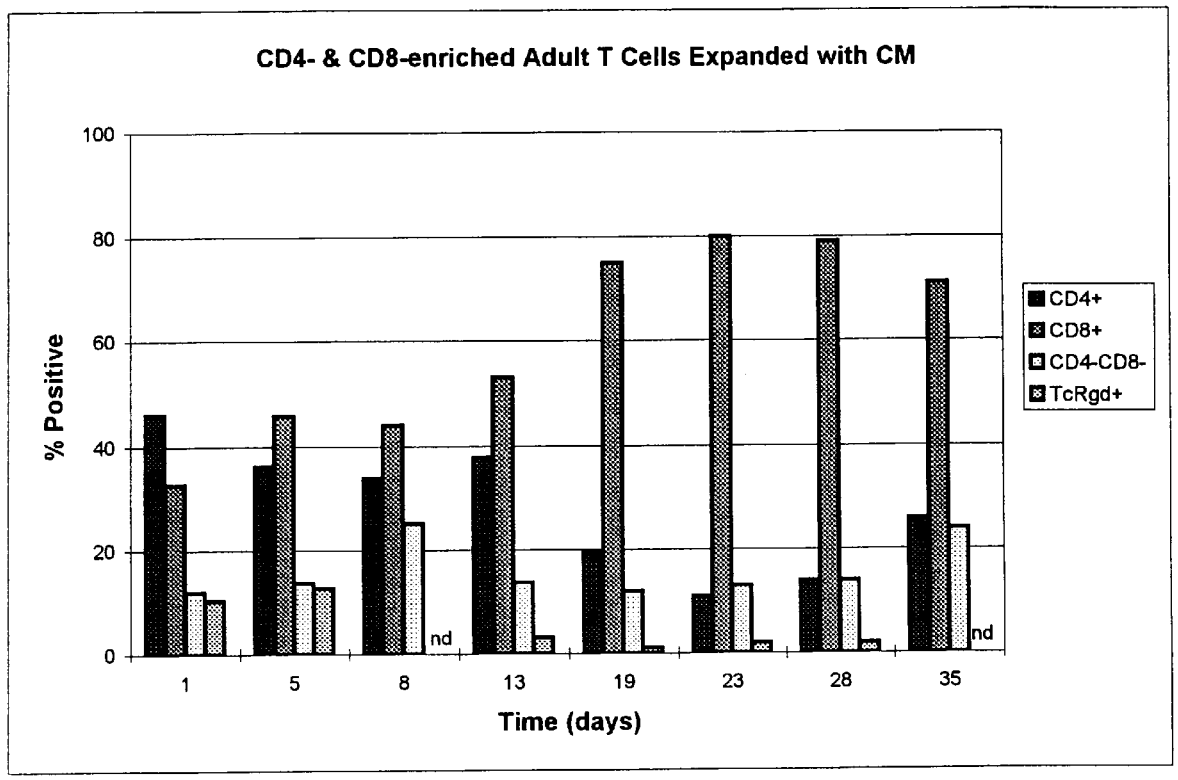
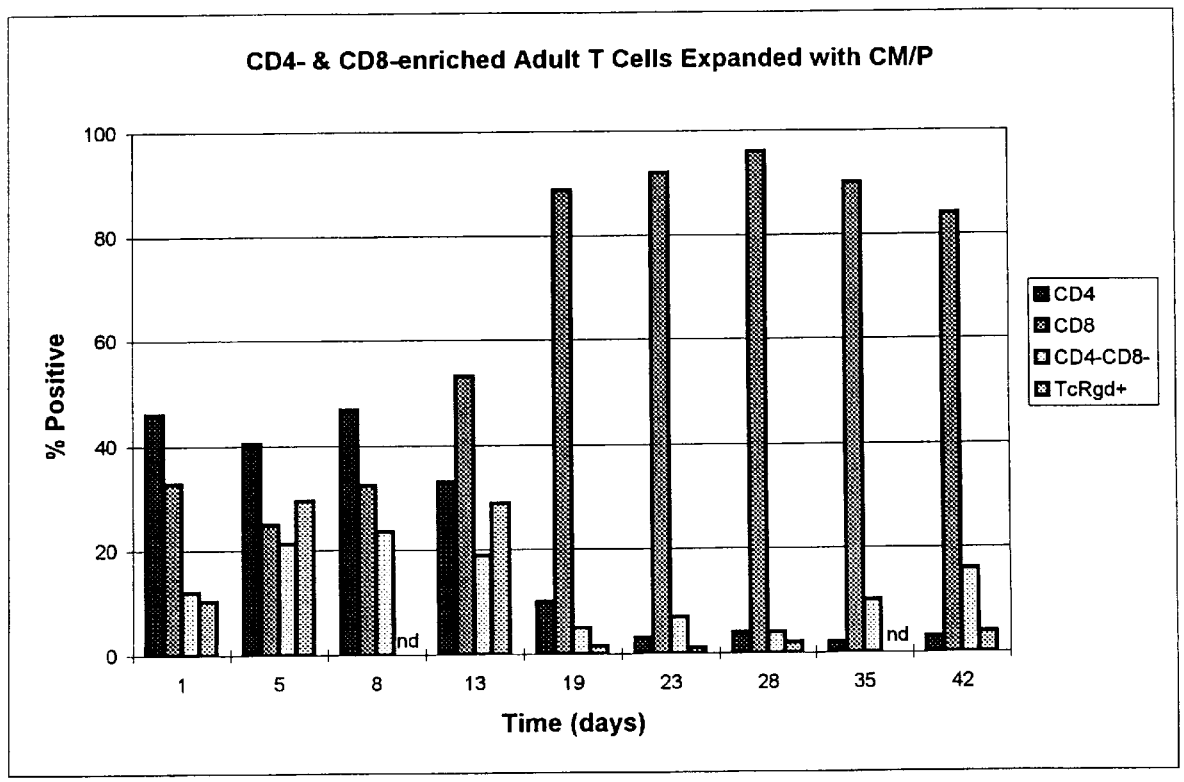

Figure 11: Polyclonal Expansion of CD+ T-Cells by CM

Figure 12: Polyclonal Expansion of CD8+ T-Cells by CM/P

Figure 18. Average per cent of CD4+, CD8+, CD4+8+, and CD4-8- Adult Blood Cells during Culture with CM Figure 20
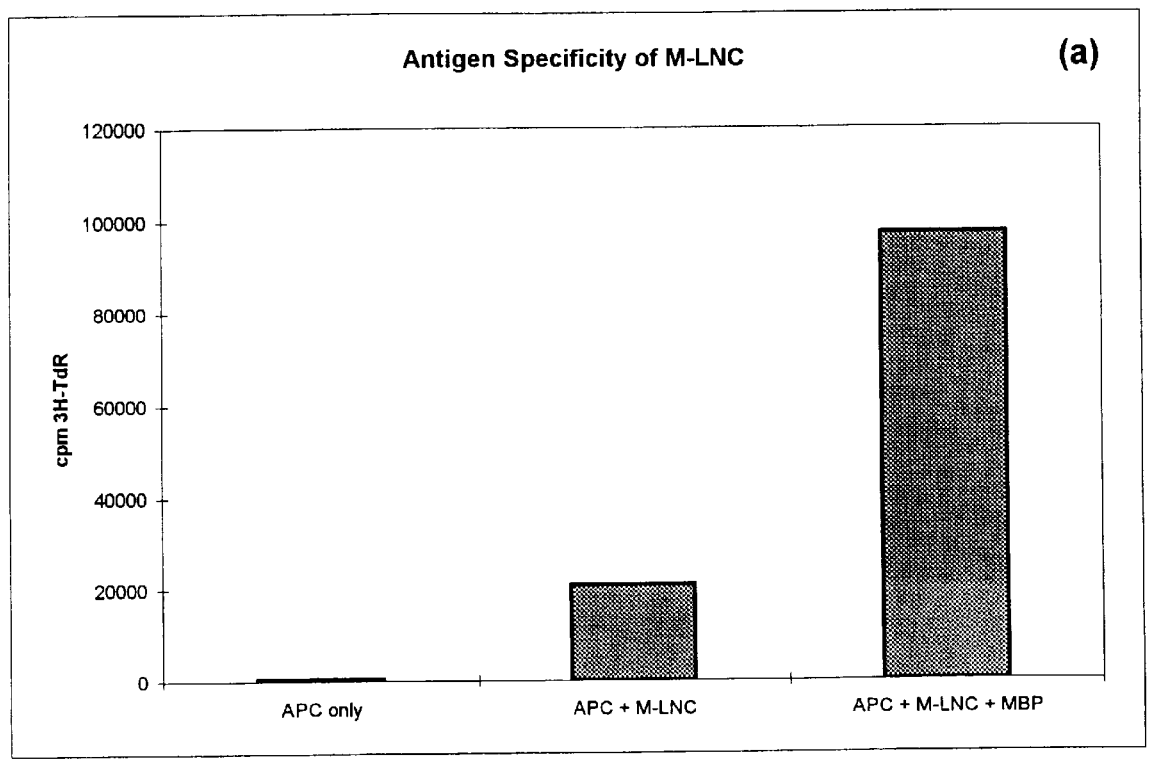
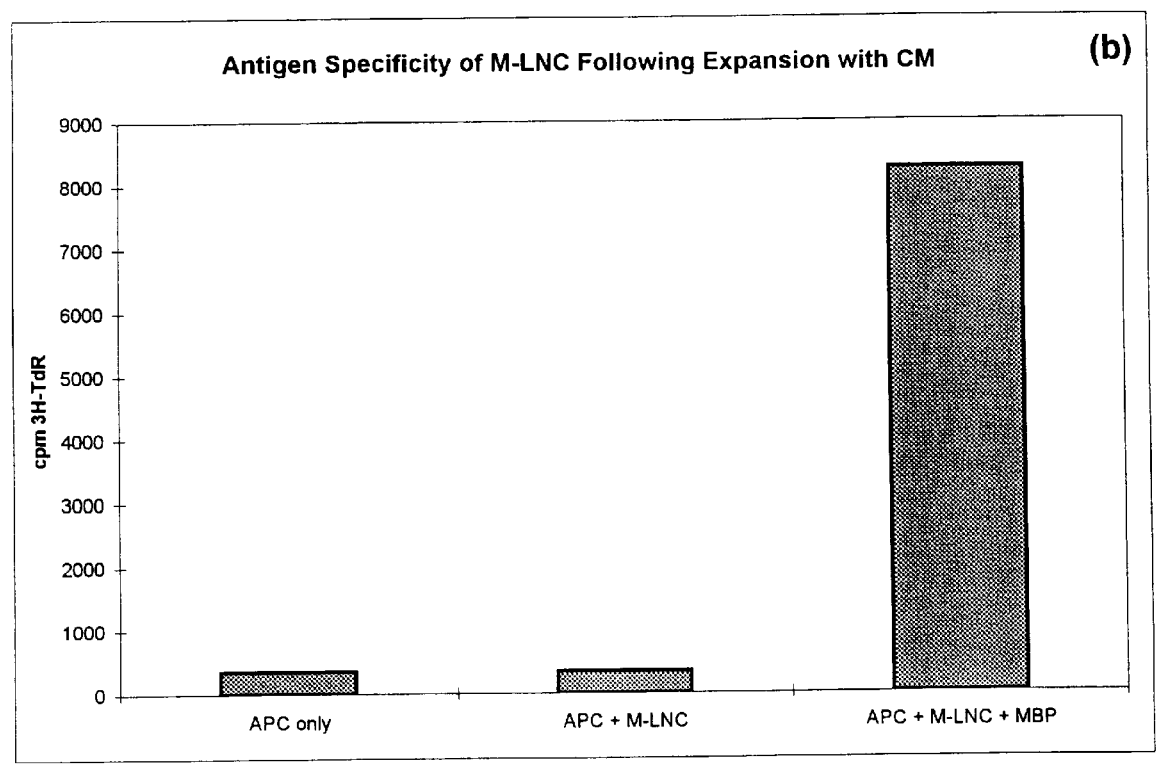

METHODS FOR THE SELECTIVE EXPANSION OF LYMPHOCYTES BY IN VITRO CULTIVATION

The present application claims priority from provisional application Ser. No. 60/037,245, filed Jan. 31, 1997.

BACKGROUND OF THE INVENTION

1. Field of the Invention

The invention relates to methods for the selective production of cells of the lymphohematopoietic system by culturing a mixed population of cells with a conditioned medium. The invention also relates to cells selectively produced by these methods and to methods for utilizing these cells.

2. Description of the Background

The human immune system uses several methods to prevent infection by foreign organisms. Skin, for example, provides a physical barrier to penetration while blood contains specialized white blood cells which function to recognize and destroy foreign pathogens. Neutrophils and macrophages are white blood cells attracted to sites of infection where they engulf and digest (phagocytose) foreign organisms, and initiate a typical inflammatory response. Blood also contains lymphocytes which provide specific and long-lasting immunity against a variety of infectious agents. B cells are lymphocytes which secrete antibodies that bind to and inactivate foreign agents within the bloodstream while T cells are lymphocytes that recognize and kill host cells that are infected by such foreign agents. T cells also recognize alterations in normal cellular proteins that are often associated with transformation to a cancerous state. Other lymphocytes called natural killer cells are specialized for the destruction of virally-infected and tumor cells. Thus, lymphocytes mediate a specific immune response and may play an important role in the prevention of cancer. Collectively, all cells of the immune system work in a coordinated manner to provide the body with a powerful and diversified repertoire of both nonspecific and highly specific weapons to combat foreign agents. For example, macrophages secrete factors that activate T cells, direct T cell responses toward specific foreign targets and phagocytose bacteria coated with antibody produced by B cells. Specialized T cells also secrete factors that determine whether the immune response will be dominated primarily by the production of antibodies or the generation of killer T cells. The concerted action of all cells of the immune system provides a rapid response to the entry of infectious agents as well as long-lasting immunity against re-exposure to the same agents.

Lymphocytes are short-lived cells produced from bone marrow stem cells that give rise to B cells, T cells and natural killer (NK) cells, in addition to all other blood cells. A key feature of stem cells is their ability to provide a constant source of progenitor cells that possess a high proliferative capacity, but are committed to produce cells of one or more blood cell lineage. Cells of the immune system are collectively referred to as lymphoid cells and are believed to be descended from a common lymphoid progenitor cell. Lymphoid progenitors are eventually restricted to the production of a single type of lymphoid cell during the process of differentiation or maturation. The high proliferative capacity of lymphoid progenitor cells allows for the production of large numbers of mature lymphoid cells which under resting conditions do not divide. B cells mature in the bone marrow where they are continuously released into the blood to maintain a constant number of functional B cells. Immature T cells migrate from the marrow to the thymus where they mature and are released to maintain the peripheral T cell pool. In fact most T cells die within the thymus where immature T cells undergo a process of positive and negative selection in the process of being educated to recognize only foreign, but not self-derived antigens. Mature NK cells formed in the bone marrow and are released into the bloodstream. Upon stimulation, virgin (naive) B and T lymphocytes undergo rapid proliferation and differentiation into both effector cells which mediate a rapid immune response and memory cells which may survive for many years before being called upon to mediate an immune response. Although NK cells can be activated by exposure to certain growth factors, they also provide an innate and spontaneous immunity against virally-infected and malignant cells.

B cells secrete antibodies which are capable of recognizing a vast number of chemical determinants found in proteins, carbohydrates, lipids, or other macromolecules, all of which are collectively referred to as antigens. Antibodies may reside on virgin or memory B cell membranes as antigen receptors which, when bound by the matching antigen, stimulate the proliferation and differentiation of B cells into short-lived plasma cells that secrete large amounts of soluble antibodies specific for the inducing antigen. Antibody binding can have a variety of effects including the sequestration and inactivation of toxic agents, the prevention of viral entry into host cells or the promotion of phagocytosis of infectious agents by macrophages. The release of antibody into the blood and other body fluids by B cells is the principal source of the humoral immune response. B cells also function, like macrophages, to present foreign antigens in a manner that can be recognized by T cells. B cells also release important growth factors that influence the function and activation of other immunologically important cells.

T cells recognize antigenic determinants through a surface receptor called the T cell receptor (TcR). Although similar in function to surface bound immunoglobin, T cell receptors are not secreted. T cells mediate their prime immunological function through direct contact with infected host cells. These infected cells cooperate by displaying (presenting) antigenic fragments of foreign proteins on their surface as a means of signaling to T cells that they are infected. While T cells recognize antigens presented on all host cells, T cells are first activated to recognize these antigens by specialized antigen-presenting cells such as dendritic cells, B cells and macrophages. Antigen-presenting cells also express co-stimulatory molecules on their surfaces which are required for full T cell activation. Together with macrophages, T cells are the main component of the cell-mediated immune response and, through the release of soluble factors, are required for virtually all aspects of the immune response. In addition to the T cell receptor, T cells are characterized by two major T cell-specific surface markers, CD4 and CD8, which define functionally distinct T cell populations. CD4 T cells, called T helper cells, are activated through interaction with antigen-presenting cells and function primarily to activate CD8 T cells, also known as cytotoxic or killer T cells (CTL). CTLs are the main effector T cell mediating the destruction of infected host cells and only recognize foreign antigens that are bound to specialized molecules found on virtually all cells. Thus, most infected cells of the body may serve as CTL targets. Target cells are killed by factors released from CTLs that cause rapid target cell lysis or through the induction of a highly ordered program of events leading to cell death. In addition to activating CTLs, CD4 helper cells also regulate B cell activation through the release of soluble factors. Like B cells, most resting virgin T cells are short-lived unless activated to proliferate and generate both effector and memory T cells.

T helper cells are grouped according to the type of soluble growth factors secreted after activation by specific antigens. T helper 1 ($T_H1$) cells secrete the main T cell growth factor, interleukin 2 (IL-2) plus interferon gamma (IFNγ) and interleukin 12. This combination of growth factors selectively activates cytotoxic T cells leading to a predominately cell-mediated immune response. T helper 2 ($T_H2$) cells secrete mainly IL-4 and IL-5 which stimulate B cells and promote a predominately humoral (antibody-based) immune response. $T_H1$ growth factors such as IFNγ block the $T_H2$ immune response while $T_H2$ factors such as IL-4 block the $T_H1$ response. Although the method of $T_H1/T_H2$ selection is not known, the type of immune response to a foreign agent is largely determined by the activation of either $T_H1$ or $T_H2$ helper T cells.

Natural killer cells do not require presentation of foreign or tumor-derived antigens on target cells to direct their cytotoxic action. NK cells possess a spontaneous cytotoxicity against a range of virally-infected and tumor cells that can be broadened following exposure to IL-2. Such cells are then called lympholine-activated killer (LAK) cells. NK cells also bind antibody-coated cells and mediate a form of cell killing called antibody-dependent cell-mediated cytotoxicity. Little is known about the nature of the markers on cells that stimulate NK cells. However, NK cytotoxicity is specifically inhibited by markers carried by most normal host cells. NK cells also produce a number of growth factors with wide ranging immunological and hematopoietic activity.

Although foreign agents such as viruses, bacteria, parasites and other microorganisms that gain entry into the body can remain extracellular, many infect only selected tissues or cells. Viruses, for example, are dependent upon specific host cells for the completion of their life cycle. It is the destruction of the host cell by the virus during its replication and the release of its progeny that leads to the clinical manifestations of the viral disease. Virally-infected cells possess a defensive mechanism whereby fragments of virus-specific proteins (peptides) are presented on their surfaces. Presentation is designed to activate T cells and elicit an immune response that includes destruction of the virally-infected host cells by $CD8^+$ cytotoxic T cells. $CD4^+$ T cells are activated by specialized antigen presenting cells and are essential for the full activation of virus-specific CTLs. Prior exposure to and recovery from an infectious agent produces memory T cells which can persist for many years and are able to mount a rapid and effective immune response upon re-exposure to the same virus. The generation of activated memory T cells, or antigen-specific T cells by ex vivo manipulation of patient T cells, offers much promise in the treatment of certain infectious diseases for which either effective vaccines have yet to be developed or existing drugs have proved to be ineffective. Such ex vivo manipulation makes it possible to boost an endogenous memory immune response in susceptible individuals or in patients who are immunocompromised, as a means of treating of infectious diseases.

Cancer is a disease which can be broadly characterized by uncontrolled cell proliferation. Normally cell growth and differentiation are highly regulated processes designed to maintain a constant number of cells to meet the particular needs of the body. Many cells reside for long periods of time as a functional part of a tissue or organ where they are terminally differentiated and incapable of cell division. Other cells such as those of the blood, immune and gastrointestinal systems are generally short-lived and require a constant supply of new cells. Such tissues that show a high rate of proliferation are most susceptible to the accumulation of alterations that can lead to cellular transformation and a cancerous state. In these cases, the normal control of cell proliferation is dysregulated leading to the over production of cells. Leukemias are cancers of the white blood cells in which the over production of such cells leads to the concomitant clinical manifestations of the disease. The proliferation of cells in solid tissue result in tumors that may be benign or malignant. Malignant tumors, the most aggressive forms of solid tumors, are characterized by the shedding or migration of malignant cells to other parts of the body facilitating the rapid spread of the cancer and ultimately resulting in poorer prognosis for the patient. The same attributes that cancer cells acquire to mediate their ability to grow and spread are often associated with the expression of altered or novel surface markers recognized by cells of the immune system. Thus, cytotoxic T cells may be activated by specific tumor markers (antigens) and subsequently kill the tumor cells in a manner analogous to cells infected by a virus. Natural killer cells also possess a potent tumor killing activity that does not appear to require the expression of specific tumor-derived markers. Although, a role for both T cells and NK cells in the destruction of tumor cells in vivo by a system of immune surveillance is not firmly established, in vitro studies have demonstrated their ability to recognize and destroy tumor cells. Thus, the ability to activate the immune system ex vivo and to direct the system to recognize specific tumor antigens has potential therapeutic benefit in the treatment of cancers for which conventional therapies have proven ineffective.

Autoimmune diseases are caused by inappropriate immune responses directed against an individual's own tissues and cells. These diseases are characterized by a variety of symptoms including chronic inflammation and the infiltration of normal tissue by activated lymphocytes that mediate an immune response leading to tissue destruction and the manifestations of disease. Examples of autoimmune disease include rheumatoid arthritis, systemic lupus eiythematosus, multiple sclerosis and type I diabetes. Certain forms of autoimmune disease are mediated by self-reactive T cells that recognize endogenous antigens normally expressed on host cells in a manner analogous to the recognition of viral antigens. Although the precise mechanism underlying activation of cytotoxic T cells against host tissue are complex and poorly understood, generally, treatments that specifically suppress these pathogenic self-reactive T cells are of benefit in the treatment of autoimmune diseases.

Cell therapy involves removing cells from a patient, modifying the cells outside of the body (ex vivo) and reinfusing the modified cells as a treatment for disease. Adoptive immunotherapy involves the removal of cells of the immune system and activating, expanding or directing these cells to recognize and kill specific targets upon reinfusion. Manipulations of human T cells include expanding cell numbers, activating cells with selected growth factors and directing cells to recognize specific foreign or tumor antigens on infected or tumor cells, respectively. Memory T cells which may be present in small numbers or which respond poorly to viral or tumor antigens in some patients may be expanded ex vivo and activated to induce a more potent killing ability. Alternatively, patient CD8 cytotoxic T cells can be expanded ex vivo and directed to kill cells expressing specific viral or tumor antigens by using an in vitro antigen-presenting system. In diseases such as AIDS in which the immune system is deficient due to the selective loss of $CD4^+$ T cells as a result of HIV infection, specific $CD8^+$ CTLs generated ex vivo may possess a more potent killing activity against virally-infected cells as a means of preventing further virus spread. $CD8^+$ CTLs may have use in the treatment of AIDS and other infectious diseases or malignancies while the $CD4^+$ cells may also have applications in reconstituting an effective immune system in AIDS patients. Alternatively, the activity of specific T cells can be reduced as a means of treating some forms of autoimmunity and facilitating organ transplantation.

Leukocytes express a variety of surface molecular markers that provide a basis for distinguishing progenitor and mature cells. The cluster of differentiation (CD) numbering system has been devised to provide a universal means for identifying various types of leukocytes. Surface markers on leukocytes are antigenic and can be bound by monoclonal antibodies. By agreement, CD numbers have been assigned to those surface markers to which are bound antibodies having similar specificity characteristics. For example, T cells were found to be distinguished from B cells by their ability to bind to sheep eryftirocytes via the CD2 surface marker. Thus, CD2 is a marker for T cells. Of course, the primary surface marker distinguishing T cells is the T cell antigen receptor (TcR), which forms a complex with another T cell specific surface marker, CD3. Most T cells express a T cell receptor composed of an alpha ($\alpha$) chain and a beta ($\beta$) chain (TcR$\alpha\beta$), while a small subset express a TcR composed of a gamma ($\gamma$) chain and a delta ($\delta$) chain (TcR$\gamma\delta$).

With regard to T cells specifically, the vast majority of T cells can be subdivided into either CD4+ or CD8+ cells, i.e. T cells which express either the CD4 or the CD8 marker. CD4+ T cells are also known as helper T cells, and function to positively or negatively influence the immune response of B cells and other T cells. CD8+ T cells are called cytotoxic or killer T cells. Suppressor T cells, which are activated by CD4+ cells, also are CD8+. Other lymphocytes which exhibit a cytotoxic function include natural killer (NK) cells and lymphokine activated killer (LAK) cells, which cells are both CD4– and CD8–, cytokine induced killer cells (CIK) which co-express CD56, CD3, TcR$\alpha\beta$ and CD8, and TcR$\gamma\delta$+ cells which are either CD4–/CD8– or CD4–/CD8+.

SUMMARY OF THE INVENTION

The present invention overcomes the problems and disadvantages associated with current strategies and designs and provides new compositions and methods for the production and use of selected populations of lymphocytes.

One embodiment of the invention is directed to methods for rapidly producing a desired population of lymphocytes. Using this method, large populations of lymphocytes can be easily, inexpensively and rapidly produced from a very small sample of cells or tissue. Lymphocyte populations can be maintained in culture, expanded, stored for later use, stimulated to differentiate or activated or directed to a specific function or target as needed. The procedures described herein are short, straightforward and applicable to lymphocytes from any source. Lymphocytes produced by the current invention are useful in transplantation therapy and provide a number of advantages over current procedures to produce such cells. The invention obviates the need to use multiple pools of donor cells and to employ extensive separation procedures, both of which are presently required to obtain enriched populations of CD4, CD8 or NK lymphocytes. Further, these methods enable the production of large numbers of CD4 and CD8 lymphocytes as well as NK cells, CIK cells, TcR$\alpha\beta$ and TcR$\gamma\delta$ T cells for use in autologous or allogeneic transplantation therapy.

Another embodiment of the invention is directed to methods for producing an expanded culture of lymphocytes containing an enriched fraction of a desired population of lymphocytes. According to these methods, a culture of cells is enriched in the lymphocyte fraction by culturing in the presence of a conditioned medium (CM) which provides a balance of stimulatory and inhibitory factors that favour the proliferation of the target lymphocyte population. The target lymphocyte population comprises populations of CD4 and CD8 lymphocytes, natural killer cells, LAK cells, CIK cells, TIL cells (tumor infiltrating cells), TcR$\alpha\beta$ and TcR$\gamma\delta$, their subpopulations, precursors and cells in intermediate stages of differentiation, terminally differentiated cells or mixtures thereof. The target cells are subsequently useful in transplantation therapy.

Another embodiment of the invention is directed to cells produced by the above-described methods. Cells can be maintained or expanded in culture, isolated and purified or cryopreserved, either before or after purification, for later use. As cells are expanded from a single population, homogeneity can be easily determined.

Another embodiment of the invention is directed to CM compositions comprising a mixture of cell factors having a balance of stimulatory and inhibitory effects favoring the proliferation of a desired cell population. The CM composition is produced by treating a cell population with an inducing agent which preferably comprises a mitogen. Useful mitogens include plant lectins such as concanavalin A (ConA) or phytohemagglutinin (PHA), T-cell mitogens such as mezerein (Mzn) or tetradecanoyl phorbol acetate (TPA) or a T-cell antibody such as those directed against the CD3 or CD28 antigen. CM can be selectively modified by removing or adding specific factors to favour the proliferation of a different target cell population. Alternatively, a CM can be prepared from a variety of different starting cell populations, thereby creating a CM-1, a CM-2, and so on, each specific for one or more different target cell populations.

Another embodiment of the invention is directed to methods of transplantation therapy wherein primary mammalian lymphocytes (e.g. from blood, other bodily fluids or tissues) are cultured in vitro with a CM. The resulting expanded lymphocytes are maintained or cryopreserved for later use or can be immediately introduced into a patient for transplantation therapy or other therapeutic or prophylactic uses. Target lymphocytes can be used to supplement defective immune systems, repair damaged immune systems or suppress overactive immune systems as a means of treating the associated diseases. Alternatively, target cells can be employed to produce useful cell products such as cytokines, lymphokines and chemokines as well as other stimulatory or inhibitory cellular factors.

Another embodiment of the invention is directed to methods of gene therapy. Target lymphocytes are made by the method of the invention and directly transfected with a genetic sequence or infected with recombinant viral vectors containing a genetic sequence. Cells which properly express the genetic sequence of interest are selected, isolated and expanded in vitro. The expanded cells expressing the gene of interest are then administered into the patient. Useful genes for gene therapy include genes whose expression products are absent or defective in the patient, and genes and other genetic sequences whose expression provide a beneficial effect to the patient.

Other embodiments and advantages of the invention are set forth, in part, in the description which follows and, in part, will be obvious from this description or may be learned from the practice of the invention.

DESCRIPTION OF THE DRAWINGS

FIG. 1 Cumulative cell yield (*a*) for cord blood cells expanded with CM, (*b*) cord blood expanded with CM/P, (*c*) adult blood cells expanded with CM. (*d*) adult blood cells expanded with CM/P, and (*e*) best fit average.

FIG. 4 Average percent of CD3+, CD4+ and CD8+ cord blood cells during culture with CM/P.

FIG. 5 Average percent of CD3+, CD4+ and CD8+ cord blood cells during culture with CM.

FIG. 6 Expansion of umbilical cord blood T cell subsets with CM and CM/P.

FIG. 7(*a*) CD4-enriched cord T cells expanded with CM and CM/P, (*b*) CD8-enriched cord T cells expanded with CM and CM/P, (*c*) unfractionated cord LDMNC expanded with CM and CM/P, and (*d*) CD4-enriched and CD8-enriched cord T cells expanded with CM and CM/P.

FIG. 8 Expansion of adult peripheral blood T cell subsets with CM and CM/P.

FIG. 9(*a*) CD4-enriched adult T cells expanded with CM and CM/P, (*b*) CD8-enriched adult T cells expanded with CM and CM/P, (*c*) unfractionated adult LDMNC expanded with CM and CM/P, and (*d*) CD4-enriched and CD8-enriched adult T cells expanded with CM and CM/P.

FIG. 20 Antigen specificity of (*a*) M-LNC and (*b*) M-LNC following expansion with CM.

DESCRIPTION OF THE INVENTION

Figure 2:
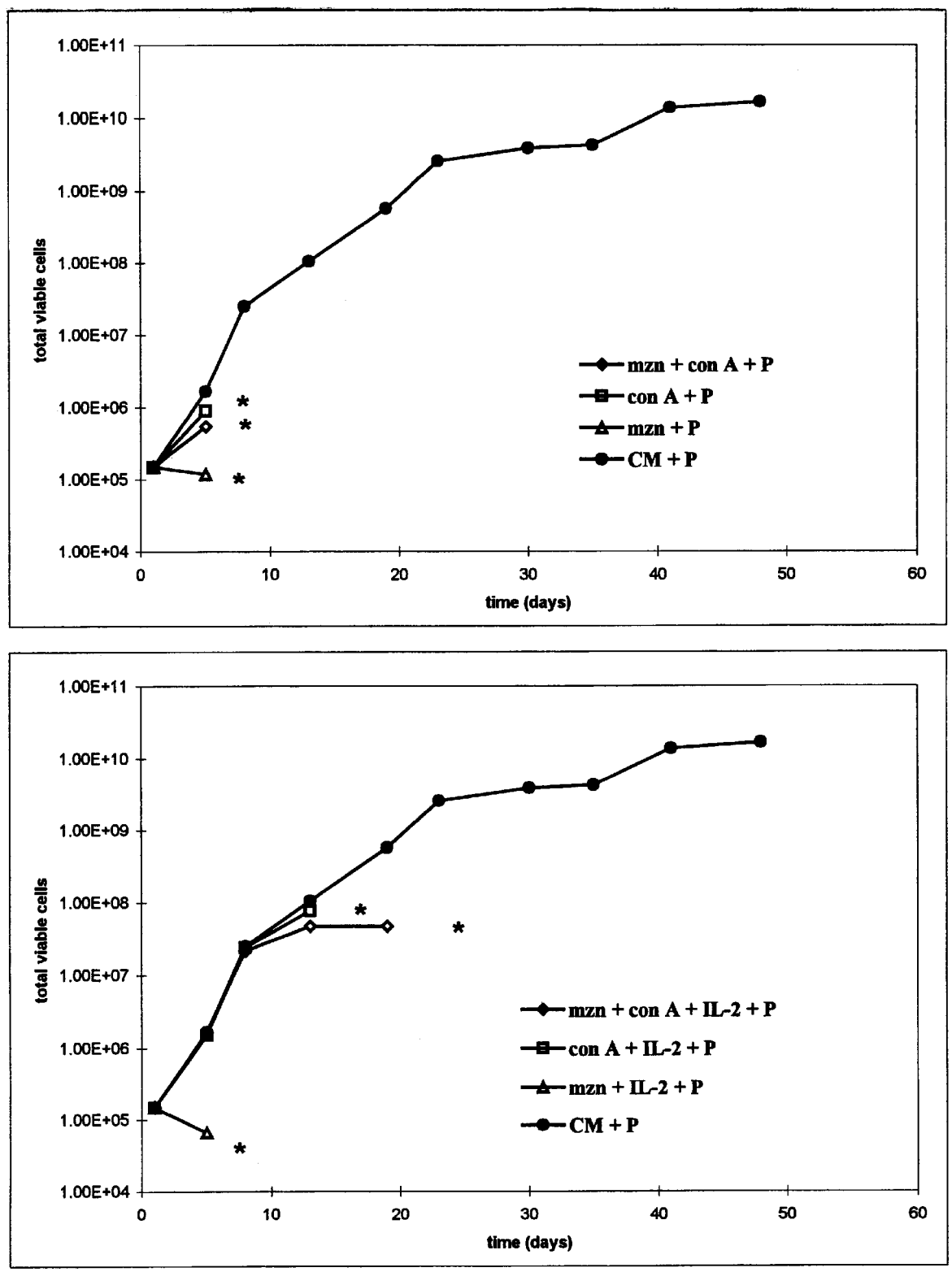
FIG. 2 Cell cultures treated with various combinations of ConA, Mzn, CM and P.

As embodied and broadly described herein, the present invention is directed to methods for the production of lymphocytes, compositions used in these methods, the resulting lymphocytes produced and methods for the use of produced lymphocytes.

Current methods of lymphocyte cell therapy cannot generate purified populations of CD4 and CD8 lymphocytes from a single unenriched lymphocyte cell population expanded in vitro. Expansion of desired lymphocyte cell populations derived from patients is often not possible, thus preventing the required therapeutic in vitro manipulation of a patient's cells. It has been discovered that large numbers of lymphocytes can be produced from very small samples of biological fluids relatively inexpensively and in a fairly short time frame. These lymphocytes, once produced, can be isolated and purified using well known and established procedures. This advantage saves the time and expense typically associated with conventional separation-enrichment techniques and provides a consistent lymphocyte source which one of ordinary skill in the art can modify to provide the appropriate cell type or the optimal level of a desired lymphocyte. The availability of such cell populations allows for not only for the complete reconstitution of the depleted, defective or missing lymphocyte population in a patient, but also provides the flexibility of having sufficient cells to permit multiple or cyclic treatments of the patient. These methods are broadly applicable to the selective expansion of several types of lymphocytes.

In the practice of the method, one or more types of lymphocyte present in a sample of cells can be preferentially expanded to enrich a specific fraction of lymphocyte. The target lymphocyte population to be expanded can be selected from any mammalian lymphocyte population, preferably a primary mammalian lymphocyte population, and more preferably a primary human lymphocyte population. The starting cell population may be, for example, a sample of a patient's blood (e.g peripheral), bone marrow, lymph or lymph node, or other cells or tissues of the lymphohematopoietic system including combinations of these cells and cell populations. Accordingly, cell populations that can be expanded and enriched in the starting population include, for example, stem cells, progenitor cells, precursor cells and fully differentiated cells (i.e. cells at all stages of differentiation), as well as combinations of these cells. For example, lymphocytes present at very low levels in some cell samples can be selectively proliferated to increase their fraction in the expanded population. During selective expansion and enrichment, nonlymphocytes can be allowed to die of or to remain unexpanded, i.e. to fall in number, proportion or both in the expanded culture. Further, expansion does not require the use of stromal or accessory feeder cells, typically necessary with conventional procedures. One of the important clinical advantages of this method is that cell populations containing a fraction of the selected lymphocytes can be produced simply and in many cases without the need for separation or purification steps or the addition of separate and expensive cytokines. The method allows for the selective and sequential production of, for example, CD4+ T cells, CD8+ T cells and CD56+ natural killer cells from a single unenriched blood or other tissue sample which then may be utilized as required by the appropriate adjustment of the culture time or conditions.

A starting cell population is selected and induced to produce a CM which comprises a mixture of cell factors secreted by or otherwise obtained from the starting cell population and which has a predetermined balance of stimulatory and inhibitory effects preferentially favoring the expansion and enrichment of the desired target cell population. The starting cell population comprises, for example, primary cells of the blood, bone marrow, body tissues or established cell lines, or cells that have been previously expanded by conventional or other means such as, for example, enriched CD4+ cells. The starting cell population may contain cells that are of the same cell type as the desired target cell, of a desired target cell type at distinct stages of differentiation and capable of differentiating to cells of the desired target cell type or cells that are of a completely different type from the desired target cell type. The invention also includes the situation where the starting cell population is the target cell population that is ultimately expanded.

The starting cell population useful to produce a particular CM for the expansion of lymphocytes is preferably selected from peripheral blood cells, umbilical cord blood cells or bone marrow cells. Because of clinical advantages, peripheral blood cells are preferred for use as a starting cell population. Peripheral blood cell populations usefull as the starting cell population include whole peripheral blood as well as fractions thereof such as, for example, leukophoresis cells, buffy coat cells, peripheral blood mononuclear cells (PBMNC), and low density mononuclear cells (LDMNC).

Production of a CM useful in the invention is accomplished by inducing the starting cell population to produce a specific mixture of factors. Preferably, the starting cell population is induced by adding an inducing agent followed by culturing. The CM inducing process may be affected by factors produced by the cells during culture, and by culturing conditions, such as, the medium used, temperature, time of culture, pK, exogenous recombinant growth factors, nutrients, etc. In this regard, the medium used may be serum-free.

Added inducing agents for the production of a CM generally comprise chemical or biological substances that have a mitogenic effect on the cell types of the starting cell population. These agents are administered to the medium. Administration may be periodic or in a single or relatively few doses. Administration may also be periodic after each of one or more preincubation periods. Among the classes of mitogens that are useful to induce the starting cell population are plant lectins, T cell mitogens and monoclonal antibodies, and combinations of these agents. Particular plant lectins that have the desired mitogenic activity include those derived from the following sources:

Phaseolus vulgaris (PHA, phytohemagglutinin)
Dolichos biflorus
Solanum tuberosum
Sophora japonica
Maclura pomifera
Pisum sativum
Ulex europaeus (UEA-I, U. europaeus agglutinin I)
Ulex europaeus (UEA-II, U. europaeus agglutinin II)
Arachis hypogaea
Glycine max
Canavalia ensiformis (ConA, concanavalin A)
Triticum vulgaris (WGA, wheat germ agglutinin)
Ricinus communis (RCA-I, R. comminis agglufinin I)
Lycopersicon esculentum
Phytolacca americana (PWM, pokeweed mitogen)
Listeria monocytogenes (LPS, lipopolysaccharide)

A particularly useful group of plant-derived mitogens includes PHA, ConA, mezerein (Mzn) and TPA (and related diterpene esters). TPA and some of its related compounds are as follows:

Phorbol 12-myristate-13-acetate (TPA)
Phorbol (4-O-methyl) 12-myristate-13-acetate
Phorbol (10-oxo-20-deoxy) 12-myristate-13-acetate
Phorbol 12-monomyristate
Phorbol 12, 13-didecanoate
Phorbol 12, 13-dibutyrate
Phorbol 12, 13-dibenzoate
Phorbol 12, 13-diacetate Mitogens of non-plant origin can also be used, such as Staphylococcal enterotoxin A (SEA), Streptococcal protein A, galactase oxidase and T cell antibodies such as anti-CD3 antibodies (e.g. OKT3) or anti-CD28 antibodies. Interferon-alpha (IFN$\alpha$), IFN$\beta$, and IFN$\gamma$ can also be used as inducing agents in some circumstances.

Cytokines and chemokines are produced in the CM, thus making the CM a source for the production of these molecules. While at least fourteen such factors have been identified so far, no combination of these known recombinant cytokines and chemokines can reproduce the activity of CM in the embodiments herein described.

A feature of the invention is the expansion of target cells using a CM. The first step is preferably carried out in an appropriate basal medium, which can be supplemented with one or more defined cytokines as desired for optimal or appropriate cell growth. Culture conditions for individual cell types may vary, but standard tissue culture conditions form the basis of culture treatment. Typically, cells are incubated in 5% $CO_2$ incubators at 37° C. in medium. Specific chemical agents, proteins, medium components such as insulin or plasma, and certain growth or colony stimulating factors (CSFs) may be required for the maintenance of certain cell types.

The CM can be added to the medium in an amount sufficient to obtain the desired expansion of the target cell or cells. Additive amounts will vary depending on the nature of the CM, the make-up of the cultured cell population and the culture conditions. In practice, this addition of CM is usually from about 1% to about 10% or more. Additionally, pooled human CM or plasma (e.g. autologous or allogeneic) may also be added in the range of from 0 to about 10% or more. CM and P can be prepared from the same cells, the same individuals or HLA-matched cells and used to expand cells (e.g. cord blood, T cells, etc.) from the same individual or HLA-matched cells. Accordingly, expanded cells can be administered prophylactically or therapeutically to treat the individual from which treated cells were obtained, or cells from which the CM was prepared or P was obtained, or can be pooled for administration to HLA-matched individuals.

The length of the culture steps can be varied to assist further in the selective proliferation of the target cell population. When the cell population involves cells on or induced to enter a differentiation pathway, the final target cell enrichment may depend on when the culture is terminated. Typically, the expansion of T cells involves a culturing period of at least 3 days, but more usually, at least about 14 to about 21 days. It may be advantageous to extend the culturing period to obtain certain target cells such as cytokine-induced killer cells and T$\gamma\delta$ T cells.

An added advantage of the invention is the inherent purging of tumor cells during cell expansion (e.g lymphoid or myeloid leukemias, lymphomas). It has been reported that the number of some chronic myeloid leukemic cells rapidly declines in long term culture. The purging of tumor cells during expansion according to the methods of the invention can be facilitated by the presence of cytokines such as, for example, IFN$\gamma$ or tumor necrosis factors (TNFs), and cells such as, for example, activated macrophages which have antiproliferative or cytotoxic effects on tumor cells.

Expanded cell populations can also be used to treat patients purged of a hematological malignancy or solid tumor. Expanded cells purged of tumor cells in culture can be administered to patients as a treatment or adjunct to conventional therapy such as chemotherapy or radiation therapy. T cells can be prepared that possess a desired antigen-specificity and used in prophylaxis or therapy in the treatment of viral-specific or tumor-specific disorders. Expanded cells can also be used in gene transduction to deliver genetic elements missing or dysfunctional in a patient (e.g. ADA gene). Further, populations of expanded cells, which may be antigen-specific, can be administered to reconstitute or otherwise strengthen an immune system damaged by a disease or a disorder, or even an otherwise healthy immune system.

The expanded cell population can have either a greater number of target cells (expansion) or a higher percentage of target cells (enrichment) in the final population, as compared to the original population, or both. For example, cells present in very low numbers and fractions can be expanded and enriched to give populations having greater than about 5%, preferably greater than about 20% of target cells or more preferably greater than about 50% of target cells. The target cell can be expanded to at least about 100-fold, and usually to at least about 10,000-fold or more.

The following examples illustrate embodiments of the invention, but should not be viewed as limiting the scope of the invention.

EXAMPLES

Example 1

Expansion of Umbilical Cord Blood Low Density Mononuclear Cells with CM

A. Preparation of CM

Human umbilical cord blood containing 20 units of heparin per ml was used as the starting material for the preparation of CM. A sample of the blood was diluted 1:20 with 2% acetic acid and the total number of nucleated cells determined using a hemocytometer. The average number of nucleated cells per ml of human umbilical cord blood was $1.2 \times 10^7$ and the average number of nucleated cells per umbilical cord was $6.0 \times 10^8$.

Blood was diluted in AIM-V™ media containing 20 units/ml heparin and 50 μm 2-mercaptoethanol (serum-free media: HCBM-2), to give a final concentration of $4 \times 10^6$ nucleated cells per ml. Mezerein was added, at a final concentration of 10 ng/ml and the mixture was incubated for 2 hours in a humidified incubator maintained at 37° C. and 5% $CO_2$. Concanavalin A was added to a final concentration of 20 μg/ml and the incubation was continued under the same conditions for four days. Supernatant (CM) was harvested by centrifugation of the mixture at 500×g for 30 minutes at 4° C., and stored at −20° C. Prior to use, CM was thawed at room temperature and clarified by centifiigation at 500×g for 15 minutes at 4° C., followed by filtration using a 0.22 μm syringe-mounted filter.

B. Composition of CM

The concentration of several specific cytokines and chemokines in CM were measured by enzyme-linked immunosorbent assay (ELISA). The median value for each factor is presented in Table 1. The factors fall into four categories (a–d) based on their concentration in CM:

| | |
|---|---|
| (a) >10 ng/ml: | IL-2, GM-CSF, MIP-1α, MIP-1β, RANTES |
| (b) 1–10 ng/ml: | IL-1β, IFN-γ, IL-16 |
| (c) <1 ng/ml: | IL-12, TNF-α |
| (d) <<1 ng/ml or not detectable: | IL-10, IL-4, IL-7, IL-15 |

TABLE 1

Composition of CM

| Factor | Concentration* (ng/ml) | Range(ng/ml) |
|---|---|---|
| IL-2 | 43.9 | 12–159 |
| GM-CSF | 11.0 | 0.7–24 |
| MIP-1α | 98.0 | 68–243 |
| MIP-1β | 11.2 | 1–39 |
| RANTES | 14.3 | 4–54 |
| IL-1β | 6.4 | 0.2–18 |
| IFN-γ | 3.6 | 0.6–14 |
| IL-16 | 2.1 | 0.5–6 |
| IL-12 | 0.26 | 0.07–0.8 |
| TNF-α | 0.37 | <0.001–3.4 |
| IL-10 | 0.02 | 0.007–0.2 |
| IL-4 | <0.023 | <0.023–0.07 |
| IL-7 | <0.001 | <0.001–0.24 |
| IL-15 | <0.008 | <0.008 |

* = median of n = 8–18 independent lots

C. Optimization of CM Addition Level

The optimal concentration of CM for causing the expansion of umbilical cord blood, low density mononuclear cells (LDMNC) was determined using CM prepared as described in Example 1A. Umbilical cord blood LDMNC were prepared by density gradient fractionation of whole umbilical cord blood using FICOLI-HYPAQUE™ (density: 1.077 g/ml). A volume of 15 ml of blood was layered onto an equal volume of FICOLI-HYPAQUE™ in a 50 ml conical tissue culture tube, which was centrifuged at 400×g for 30 minutes at room temperature. Low density mononuclear cells at the interface were collected, and the cells washed twice in HCBM-2 by cenftifiigation at 100×g for 10 minutes at room temperature. LDMNC were diluted in HCBM-2 containing 10% fetal calf serum and incubated in polystyrene tissue culture flasks overnight at 37° C. and 5% $CO_2$. The density gradient fractionation was repeated and the cells washed twice in HCBM-2. The yield of LDMNC was determined using 2% acetic acid as described above. The average number of LDMNC per ml of umbilical cord blood was $3.2 \times 10^6$ and the average number of LDMNC per umbilical cord was $1.1 \times 10^8$.

Umbilical cord LDMNC were diluted to a final density of $1 \times 10^5$ cells/mil in HCBM-2 containing 0–10 % CM. Cell suspensions were incubated in a 24-well tissue culture plate (1.5 ml/well) for 3 days at 37° C. and 5% $CO_2$. Cell count and viability for each condition were determined by mixing a sample of the culture with an equal volume of 0.4% trypan blue and counting the unstained (viable) and blue (nonviable) cells using a hemocytometer. As indicated in Table 2, the greatest levels of cell expansion were obtained using 5% and 10% CM.

TABLE 2

Optimization of CM Addition Level

| Percent CM | Fold Cell Expansion | Percent Cell Viability |
|---|---|---|
| 0 | 0.95 | 90 |
| 1 | 6.2 | 94 |
| 2 | 8.9 | 94 |
| 5 | 10.0 | 88 |
| 10 | 10.0 | 88 |

D. Expansion of Umbilical Cord Blood Low Density Mononuclear Cells Cultured with CM Umbilical cord blood LDMNC were prepared as described in example 1C. The cells were diluted to a final density of $1 \times 10^5$ cells/ml in serum-free HCBM-2 medium containing 5% CM. The cell suspension was incubated in a 24-well tissue culture plate (1.5 ml/well). Every 4 to 7 days the cell count and viability were determined using trypan blue as described above. At each time point, the cells were sub-cultured by diluting an appropriate volume of the cultured cells to a cell density of $1 \times 10^5$ cells/ml in fresh HCBM-2 containing 5% CM. The fold of cell expansion was determined at each passage, and the total theoretical yield of viable cells calculated assuming all of the cells had been kept in continuous culture. The data from over 50 cultures are shown in FIG. 1a. The best fit line of the average cumulative cell yield for these cultures is shown in FIG. 1e. On average, umbilical cord LDMNC cultured under these conditions expand approximately 10-fold in 5 days, and can achieve more than a 10,000-fold expansion within one month.

The addition of 5% umbilical cord blood plasma (P) to cultures of umbilical cord blood LDMNC in 5% CM (CM/P) generally increases the longevity of the cultures and can result in a further 10-fold increase in expansion (FIGS. 1b and 1e).

E. Direct Addition of ConA, Mzn and IL-2 to Umbilical Cord Blood Low Density Mononuclear Cells Umbilical cord blood LDMNC were prepared as described in Example 1C and cultured as described in Example 1D. Either 5% CM or combinations of 20 μg/ml ConA, 10 ng/ml Mzn and 10 ng/ml recombinant human IL-2 were added directly to cultures which were further supplemented with 5% umbilical cord blood plasma (P). The maximum fold of expansion obtained using the direct addition of ConA, Mzn and IL-2 (315-fold) was several orders of magnitude less than that obtained using CM (108,000-fold), indicating that the T cell expansion activity of CM was not due to the direct stimulation of the cells by residual Mzn or ConA that was used to prepare CM (FIG. 2).

F. Complementation of CM Activity

Figure 3:
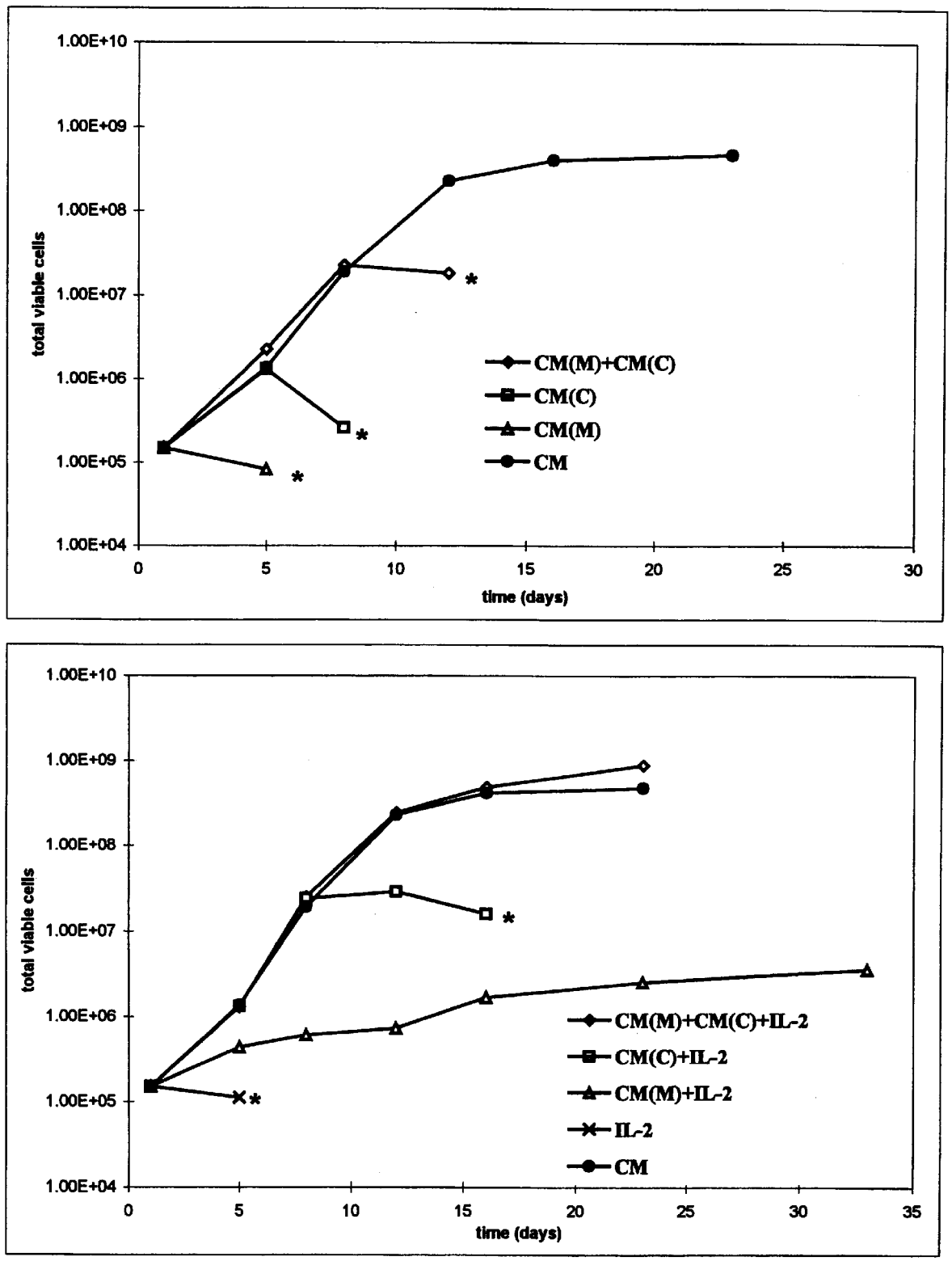
FIG. 3 Cell cultures treated with various combinations of CM, CM(C), CM(M) and IL-2.

CM, prepared using both Mzn and ConA as described in Example 1A, was compared to conditioned media (CM) prepared with ConA only (CM(C)) or with MZm only (CM(M)). Unlike complete CM, which was shown to contain significant levels of IL-2 (see Example 1B, Table 1), the component CMs, CM(C) and CM(M) did not contain detectable IL-2. Accordingly, the component CMs were supplemented with 10 ng/ml IL-2. Umbilical cord blood LDMNC were prepared as described in Example 1C and cultured as described in Example 1D in the presence of 5% CM, 5% CM(M), 5% CM(M plus IL-2, 5% CM(C), 5% CM(C) plus IL-2, 5% CM(M) plus 5% CM(C), or 5% CM(M) plus 5% CM(C) plus IL-2. Only the combination of CM(M) plus CM(C) plus IL-2 produced a level of cell expansion equivalent to complete CM (FIG. 3). Although some growth was obtained using other combinations, the overall fold of expansion was much less and the kinetics of expansion were different These results indicate that there are at least three active components in CM: one is ConA-dependent, one is Mzn dependent and one is IL-2 which is dependent on both ConA and Mzn together.

G. Expansion of Umbilical Cord Blood Low Density Mononuclear Cells Cultured with Known Mitogens In contrast to the maximum folds of cell expansion achieved by culturing umbilical cord blood LDMNC with CM or CM/P, the maximum folds of expansion achieved when the same cells are cultured in the presence of other mitogens (Table 3), or combinations thereof, are very low (Table 4). The growth factors are recombinant and the anti-CD3 monoclonal antibody, OKT3, was purified from cell culture supernatant by precipitation at 50% ammoniunm sulphate saturation. The factors were used at biologically active concentrations as indicated in Table 3. Umbilical cord blood plasma (P) at a concentration of 5%, was added to most cultures involving mitogen stimulation.

TABLE 3

Concentrations of Mitogens Used to Stimulate Cord Blood Low Density Mononuclear Cells

| | |
|---|---|
| IL-2 | 0.6–15 ng/ml |
| IL-1β | 0.03–2 ng/ml |
| IFN-γ | 0.1–10 ng/ml |
| GM-CSF | 0.6–12 ng/ml |
| TNF-α | 0.02–10 ng/ml |
| MIP-1α | 3.4–68 ng/ml |
| MIP-1β | 0.75–15 ng/ml |
| RANTES | 3–60 ng/ml |
| IL-3 | 10 ng/ml |
| erythropoietin | 2 U/ml |
| SCF | 25 ng/ml |
| IL-4 | 10 ng/ml |
| IL-10 | 0.005 ng/ml |
| IL-12 | 0.08–10 ng/ml |
| OKT3 | 10–1000 ng/ml |
| mezerein | 0.5 ng/ml |
| concanavalin A | 1 μg/ml |

TABLE 4

Expansion of Umbilical Cord Blood Low Density Mononuclear Cells Cultured with Known Mitogens

| Mitogen Combination | Maximum Fold Cell Expansion |
|---|---|
| IL-2/P | 6 |
| IL-2/IL-1β/IFN-γ/P | 9 |
| IL-2/IL-1β/IFN-γ/GM-CSF/P | 11 |
| IL-2/IL-1β/IFN-γ/GM-CSF/ /TNF-α/P | 17 |
| IL-2/IL-1β/IFN-γ/GM-CSF/ /TNF-α/MIP-1α/MIP-1β/RANTES/P | 56 |
| IL3/erythropoietin | 2 |
| IL3/SCF/erythropoietin | 12 |
| IL-4/P | 2 |
| IL-2/IL-4/P | 11 |
| IL-2/IL-12/P | 10 |
| IL-4/IL-12/P | 7 |
| IL-2/IL-4/IL-12/P | 9 |
| OKT3/FBS | 38 |
| OKT3/IL-2/FBS | 30 |
| OKT3/IL-2/P | 13 |
| Mzn/P | <1 |
| Mzn/IL-2/P | <1 |
| ConA/P | 6 |
| ConA/IL-2/P | 3052 |
| ConA/IL-2/IL-1β/P | 2056 |
| ConA/IL-2/IL-1β/MIP-1α/P | 237 |

TABLE 4-continued

Expansion of Umbilical Cord Blood Low Density
Mononuclear Cells Cultured with Known Mitogens

| Mitogen Combination | Maximum Fold Cell Expansion |
|---|---|
| Mzn/ConA/P | 4 |
| Mzn/ConA/IL-2/P | 315 |
| ConA/IL-2/IL-1β/IL-12/IFN-γ/ /GM-CSF/TNF-α/MIP-1α/MIP-1β/ /RANTES/P | 911 |
| ConA/IL-2/IL-1β/IL-12/IL-10/IFN-γ/ GM-CSF/TNF-α/MIP-1α/MIP-1β/ /RANTES/P | 47 |

Example 2

Expansion of Adult Peripheral Blood Low Density Mononuclear Cells with CM

A. Expansion of Adult Peripheral Blood Low Density Mononuclear Cells with CM

Low density mononuclear cells were isolated from human adult peripheral blood by density gradient centrifugation using the same technique described for umbilical cord blood in Example 1C. The average number of nucleated cells per ml of adult peripheral blood was $5.6 \times 10^6$ and the average yield of LDMNC per ml of adult peripheral blood after density gradient fractionation was $1.2 \times 10^6$.

Adult peripheral blood LDMNC were cultured at $1 \times 10^5$ cells/ml in HCBM-2 containing 5% CM as described for umbilical cord blood cells in Example 1D. Data from over 18 cultures of adult LDMNC are shown in FIG. 1c. The best fit line of the average cumulative cell yield for these cultures is shown in FIG. 1e. Expansion of adult peripheral blood cells in 5% CM is routinely greater than that of umbilical cord blood cells under the same conditions. On average, adult peripheral blood mononuclear cells cultured under these conditions expand approximately 10-fold in 5 days, and often exceeds a 100,000-fold expansion within one month. The addition of 5% umbilical cord blood plasma does not increase the expansion of adult peripheral blood LDMNC cultured in 5% CM (FIGS. 1d and 1e).

B. Comparison of Umbilical Cord Blood and Adult Peripheral Blood Lymphocyte Expansion by CM and CM/P Table 5 compares the average fold expansion of T cells from umbilical cord blood LDMNC and adult peripheral blood LDMNC. CM is capable of reproducibly inducing a very large expansion of umbilical cord blood cells and an even larger expansion of adult peripheral blood cells. The addition of umbilical cord blood plasma (P) tends to increase the expansion of cord cells and extend the longevity of the cultures. Adult peripheral blood cells are less dependent on cord blood plasma (FIG. 6). The average folds of cell expansion are significantly greater than the maximum fold of cell expansion achieved by any other mitogens (Table 4).

TABLE 5

Comparison of Umbilical Cord Blood and Adult Peripheral
Blood Lymphocyte Expansion by CM and CM/P

|  | Umbilical Cord Blood | | Adult Peripheral Blood | |
|---|---|---|---|---|
|  | CM (n = 29) | CM/P (n = 24) | CM (n = 13) | CM/P (n = 12) |
| Average fold expansion in 4 weeks | 7,948 | 30,621 | 182,227 | 128,719 |
| Range | 215–42,004 | 112–196,130 | 2,768–1,349,147 | 1,918–1,033,200 |
| Percent that expanded beyond 4 weeks | 66 | 88 | 92 | 92 |

Example 3

Comparison of Buffy Coat CM and Whole Blood CM, and Cord Blood CM and Adult Blood CM CM prepared from whole, unfractionated umbilical cord blood as described in Example 1A, was compared to CM prepared from buffy coat cells. Umbilical cord blood was centrifuged at 400×g for 15 minutes at room temperature. The buffy coat layer of predominantly leukocytes, together with the supernatant plasma, was collected and the total number of nucleated cells was determined using 2% acetic acid as described in Example 1A. Buffy coat leukocytes were diluted in HCBM-2 to a final cell density of $4 \times 10^6$ cells/ml. Buffy coat CM was prepared by adding mezerein and concanavalin A as described in Example 1A for whole blood. Buffy coat CM and whole blood CM caused similar folds of expansion of umbilical cord blood cells when used in culture at a concentration of 5% (Table 6).

TABLE 6

Comparison of CMs

|  | Fold of Cell Expansion | |
|---|---|---|
|  | CM | CM/P |
| Buffy Coat CM vs. Whole Blood CM | | |
| Buffy Coat CM | 278,000 | 223,000 |
| Whole Blood CM | 122,000 | 287,000 |
| Cord Blood CM vs. Adult Blood CM | | |
| Cord Blood CM | 329,000 | 517,000 |
| Adult Blood CM | 52,000 | 525,000 |

Umbilical cord blood CM was also compared to adult peripheral blood CM. ELISA analysis indicated that adult peripheral blood CM has a cytokine profile that is very similar to that of umbilical cord blood CM (Example 1B, Table 1), except for a higher level of INF-γ (median=102 ng/ml, range=47–302 ng/ml). Adult peripheral blood CM and umbilical cord blood CM caused similar folds of expansion of umbilical cord blood cells when used in culture at concentrations of 5% (Table 6).

Example 4

Expression of T Cell Antigens on Cord Blood Cells and Adult Blood Low Density Mononuclear Cells The phenotype of cord blood T cells expanded with CM or CM/P was extensively characterized by one, two or three-color flow cytometry, using the combinations of fluorescent-labeled antibodies specific for the T cell markers described in Table 7.

The proportion of fresh umbilical cord blood LDMNC and the proportion of fresh adult peripheral blood LDMNC expressing each of these antigens is given in Table 8, while the proportions co-expressing CD3, CD4 and CD8 are given in Table 9.

TABLE 7

Antibody Combinations used in Flow Cytometry

| Antibody Combination | Marker | Description |
|---|---|---|
| FITC-anti-CD 8 | CD 8 | Cytotoxic T cells |
| PE-anti-CD 4 | CD 4 | Helper T cells |
| TC-anti-CD 3 | CD 3 | Pan T cells |
| FITC-anti-TcRαβ | T cell receptor αβ | Majority of T cells |
| PE-anti-TcRγδ | T cell receptor γδ | Small subset of TCRαβ |
| FITC-anti-CD 45RA | CD 45RA isoform | Naive T cells |
| PE-anti-CD 45RO | CD 45RO isoform | Memory T cells |
| FITC-anti-HLA-DP | class II MHC | Activated T cells |
| FITC-anti-HLA-DQ | class II MHC | Activated T cells |
| TC-anti-HLA-DR | class II MHC | Activated T cells |
| TC-anti-CD 25 | IL-2R α chain | Activated T cells |
| TC-anti-CD 69 | Activation inducer | Activated T cells |
| FITC-anti-CD 71 | Transferrin receptor | Activated T cells |
| FITC-anti-CD8 | CD 8 | Cytotoxic T cells |
| PE-anti-CD 56 | CD 56 | NK cells/Activated T cells |
| TC-anti-CD 3 | CD 3 | Pan T cells |
| FITC-anti-CD 8 | CD 8 | Cytotoxic T cells |
| PE-anti-CD 56 | CD 56 | NK cells/Activated T cells |
| TC-anti-TcRαβ | T cell receptor αβ | Majority of T cells |
| FITC-anti-CD 16 | Fcγ-R type IIIa | NK cells |
| PE-anti-CD 56 | CD 56 | NK cells/Activated T cells |
| TC-anti-CD 3 | CD 3 | Pan T cells |

TABLE 8

Antigen Expression (percent) on Fresh Cord and Adult Blood LDMNC

| | | Cord Blood % positive | | | Adult Blood % positive | | |
|---|---|---|---|---|---|---|---|
| Type | Description | Mean | S.D. | n | Mean | S.D. | n |
| Progenitor | CD34 | 1.6 | 1.1 | 67 | 0.9 | 0.6 | 6 |
| Leukocyte | CD45 | 81 | 16 | 52 | 85 | 20 | 3 |
| Erythroid | GlyA | 21 | 16 | 43 | | | |
| Monocyte | CD14 | 17 | 10 | 18 | | | |
| Myeloid Progenitor | CD33 | 19 | 11 | 73 | 12 | 6 | 6 |
| Early B and T Cell | CD38 | 61 | 24 | 11 | | | |
| T Cell | CD3 | 46 | 18 | 82 | 57 | 14 | 26 |
| | CD4 | 39 | 15 | 45 | 45 | 11 | 19 |
| | CD8 | 20 | 8 | 46 | 30 | 7 | 19 |
| | TcRαβ | 46 | 13 | 11 | 62 | 20 | 4 |
| | TcRγδ | 3 | 2 | 2 | 3 | | 1 |
| Naive T Cell | CD45 RA | 46 | 20 | 27 | 52 | 17 | 6 |
| Memory T Cell | CD45 RO | 30 | 14 | 21 | 52 | 8 | 6 |
| B Cell | CD19 | 19 | 14 | 20 | 18 | | 1 |
| B Cell/NK Cell | CD16 | 22 | 9 | 14 | 20 | 4 | 2 |
| NK Cell | CD56 | 5 | 4 | 23 | 7 | 4 | 8 |
| MHC II | HLA-DR | 19 | 12 | 25 | 51 | 30 | 4 |
| | HLA-DP | 24 | 8 | 5 | 50 | | 1 |
| | HLA-DQ | 17 | | 1 | 43 | | 1 |

TABLE 9

Co-expression of CD3, CD4 and CD8 (percent) on Fresh Cord and Adult Blood Low Density Mononuclear Cells

| Antigen | | | Adult | | | Cord | | |
|---|---|---|---|---|---|---|---|---|
| CD3 | CD4 | CD8 | Mean | S.D. | N | Mean | S.D. | N |
| + | | | 57 | 14 | 26 | 46 | 18 | 82 |
| | + | | 45 | 11 | 19 | 39 | 15 | 45 |
| | | + | 30 | 7 | 19 | 20 | 8 | 46 |
| + | + | | 37 | 10 | 19 | 33 | 13 | 44 |
| + | | + | 20 | 8 | 19 | 11 | 6 | 44 |
| − | + | | 3 | 2 | 19 | 4 | 2 | 43 |
| − | | + | 7 | 4 | 19 | 8 | 6 | 44 |
| + | + | + | 5 | 4 | 19 | 4 | 2 | 44 |
| − | − | − | 35 | 13 | 19 | 47 | 17 | 44 |

Example 5

Expression of CD3, CD4 and CD8 on Cord Blood LDMNC During Culture with CM/P

Umbilical cord blood LDMNC were prepared as described in Example 1C and cultured in HCBM-2 containing 5% CM and 5% P as described in Example 1D. At each passage cells were stained with fluorescent-labeled antibodies specific for the T cell surface antigens CD3, CD4 and CD8 (Table 7), and were analyzed using a COUISTER EPICS ELITE™ fluorescence-activated cell sorter (FACS). As indicated in Table 8, approximately 46% of the starting population of cells was CD3+, 39% was CD4+ and 20% was CD8+. FIG. 4 shows cord blood LDMNC cultured in CM/P over time. The percentages of CD3+, CD4+ and CD8+ cells at the outset are similar to those in Table 8. Within 5 days of culture in HCBM-2 containing 5% CM and 5% P, greater than 90% of the cells were CD3+, and the proportion of CD3+ cells remained elevated for the remainder of the culture. The percent of CD4+ T cells increased to 80% within 5 days of culture, while the percent of CD8+ T cells did not increase (~18%). CD4+ T cells continued to be the predominate cell phenotype in the culture until approximately day 14, at which point the proportion of CD8+ cells began to increase and the proportion of CD4+ T cells began to decrease. Thereafter, CD8+ T cells remained the dominant cell phenotype. Most of these cells continued to co-express CD3.

Example 6

Expression of CD3, CD4 and CD8 on Adult Blood Low Density Mononuclear Cells During Culture with CM Adult peripheral blood LDMNC were prepared and cultured in HCBM-2 containing 5% CM as described in Example 2A. At each passage, the cells were stained with fluorescent-labeled antibodies as described above. As indicated in Table 8, approximately 57% of the starting population of cells was CD3+, 45% was CD4+ and 30% was CD8+. FIG. 5 shows adult blood LDMNC cultured in CM over time. The percentages of CD4+ and CD8+ cells at the outset are similar to those in Table 8. Within 5 days of culture in HCBM-2 containing 5% CM, greater than 80% of the adult cells were CD3+, and the proportion of CD3+ cells remained elevated for the remainder of the culture. The percent of CD4+ T cells increased to 67% within 5 days of culture, while the percent of CD8+ T cells increased slightly (~34%). Similar to the pattern found with the umbilical cord LDMNC, the CD4+ T cells continued to be the predominate cell phenotype in the adult cell culture until approximately day 14, when the proportion of CD8+ cells began to increase substantially and the proportion of CD4+ T cells decreased. Thereafter, CD8+ T cells remained the dominant cell phenotype. Most of these cells continued to co-express CD3.

Example 7

Expansion and Phenotype of Enriched T Cell Subsets Cultured in CM and CM/P

Umbilical cord blood LDMNC were prepared as described in Example 1C, following which the CD4+ T cell and the CD8+ T cell subsets were enriched using a negative selection, immunomagnetic affinity technique (Stem Cell Technologies, Vancouver, BC). The CD4-enriched populations routinely contained >90% CD4+ T cells while the CD8-enriched populations routinely contained >80% CD8+ T cells. Enriched subsets were expanded with CM or CM/P as described in Example 1D before and after recombination of the enriched T cell subsets. Overall expansion of the cells was similar regardless of whether the starting population consisted of unfractionated LDMNC, CD4-ENRICHED cells, CD8-enriched cells, or recombined CD4-enriched and CD8-enriched cells (FIG. 9).

The phenotype of the expanded cells was determined as described in Example 5. In general and as expected, CD4-enriched T cells cultured with CM yielded CD4+ cells. While CD4-enriched cells cultured with CM/P also yielded mainly CD4+ cells, Tcγδ+ cells and CD56+/CD3+ cells were also produced later in culture (FIG. 7a). Similarly, CD8-enriched cells cultured in CM yielded mainly CD8+ cells while CD8-enriched cells cultured with CM/P yielded mainly CD8+ cells, but also yielded these additional populations (FIG. 7b). Unfractionated LDMNC (FIG. 7c) and recombined CD4-enriched and CD8-enriched cells (FIG. 7d) gave the expected pattern of predominantly CD4+ cells in early phase of the culture and predominantly CD8+ cells in the later phase of the culture. The addition of umbilical cord blood plasma enhanced the switch from a CD4 phenotype to a CD8 phenotype and increased the expansion of the Tcγδ+ cells and CD56+/CD3+ cells.

CD4+ T cells and CD8+ T cells were enriched from adult peripheral blood and expanded as described above with very similar results. FIG. 8 shows the expansion and FIGS. 9a–9d show the phenotype of adult peripheral blood T cell subsets cultured with CM and CM/P.

The results indicate that very large numbers of relatively pure CD4+ T cells and CD8+ T cells can be obtained from either umbilical cord blood or adult peripheral blood in a very short period of time by culturing the enriched subsets with CM and that additional populations of cells can be obtained by manipulation of culture conditions.

Example 8

Expansion of Tcαβ+ Cells and TcRγδ+ Cells with CM/P

Figure 10:
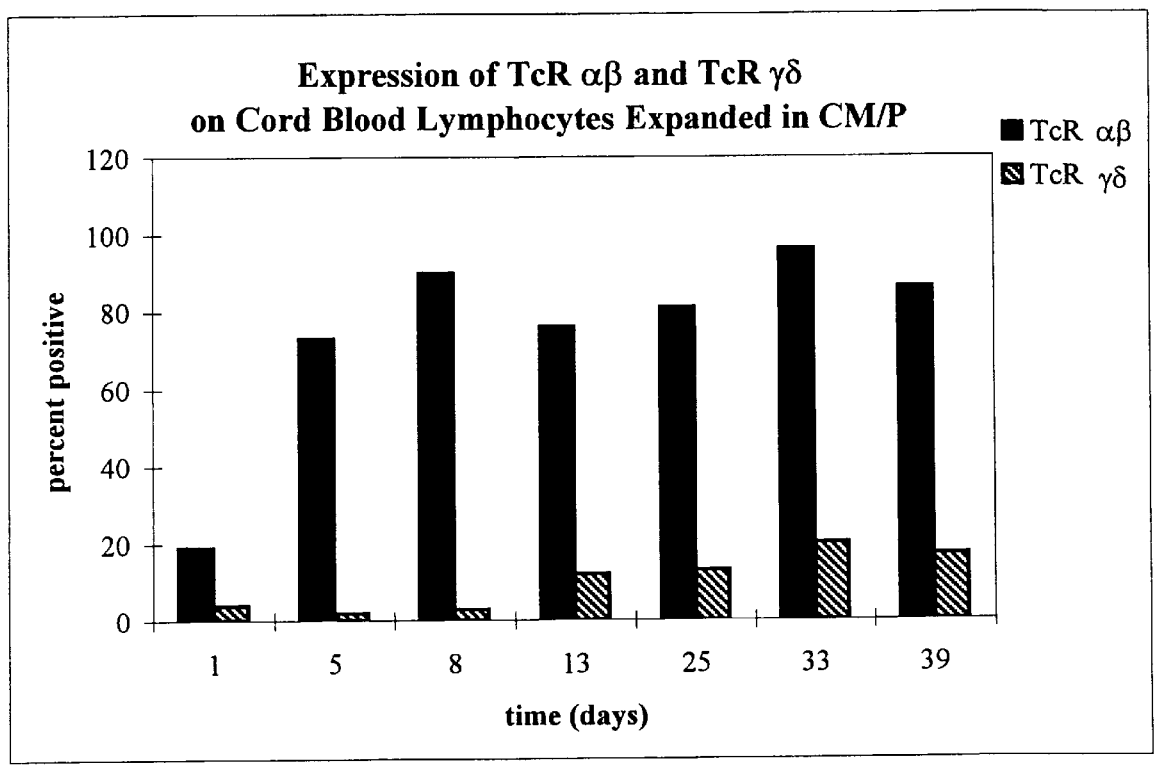
FIG. 10 Expression of Tc$\alpha\beta$, and TcR$\gamma\delta$ on cord blood lymphocytes expanded in CM/P.

Umbilical cord blood LDMNC were prepared as described in Example 1C and expanded as described in Example 1D using 5% CM and 5% P. At each time point, the expression of the T cell receptor (TcR) was examined by FACS analysis as described in Example 4 using fluorescence-labeled monoclonal antibodies specific for the alpha-beta TcR (TcRαβ) or the gamma-delta TcR (TcRγδ). Although the majority of the T cells expressed TcRαβ throughout the culture, a significant portion (about 18%) of the T cells expressed Tcγδ in the later stages of the culture (FIG. 10). The presence and proportion of Tcγδ8+ T cells varied between different experiments when unfractionated LDMNC were expanded. However, when CD4-enriched T cells (Example 7, FIG. 7a, FIG. 9a) were cultured in CM/P, the proportion of TcRγδ+ T cells was reproducibly increased (28–64%) (Table 10).

TABLE 10

Expression of TcRγδ

| Exp. | Cell Source | Enrichment | Expansion | Percent TcRγδ+ | Time |
|---|---|---|---|---|---|
| 1 | Adult | CD4 | CM/P | 28 | 23 days |
| 2 | Adult | CD4 | CM/P | 53 | 23 days |
| 3 | Adult | CD4 | CM/P | 64 | 27 days |
| 4 | Cord | CD4 | CM/P | 46 | 37 days |

Example 9

T Cell Receptor Vβ Gene usage by T Cells Expanded with CM and CM/P

Figure 11:
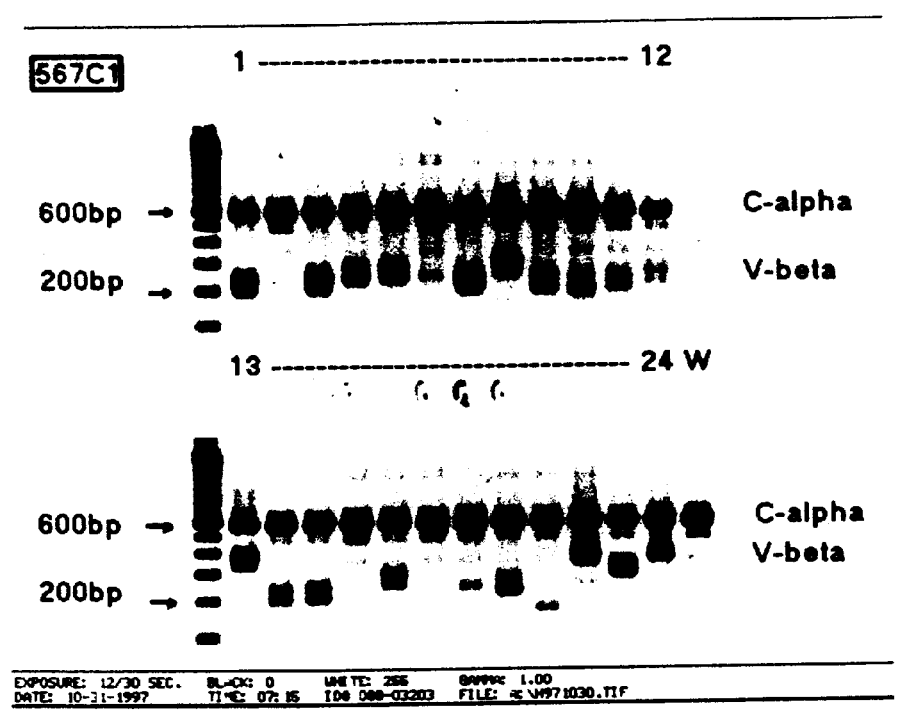
FIG. 11 Polyclonal expansion of CD4+ T cells by CM.

Adult peripheral blood LDMNC were prepared as described in Example 2 and cultured with 5% CM for 8 days. This time point represents the CD4-dominant stage (Example 6, FIG. 5). Cells were lysed and mRNA was isolated and used to prepare cDNA. cDNA was amplified by polymerase chain reaction (PCR) using primers specific for each of the 24 families of the T cell receptor Vγ chain. Agarose gel electrophoretic analysis of the PCR products revealed that all 24 Vγ genes were present (FIG. 11). These results indicate that the CD4+ T cells expanded from LDMNC with CM are polyclonal.

Figure 12:
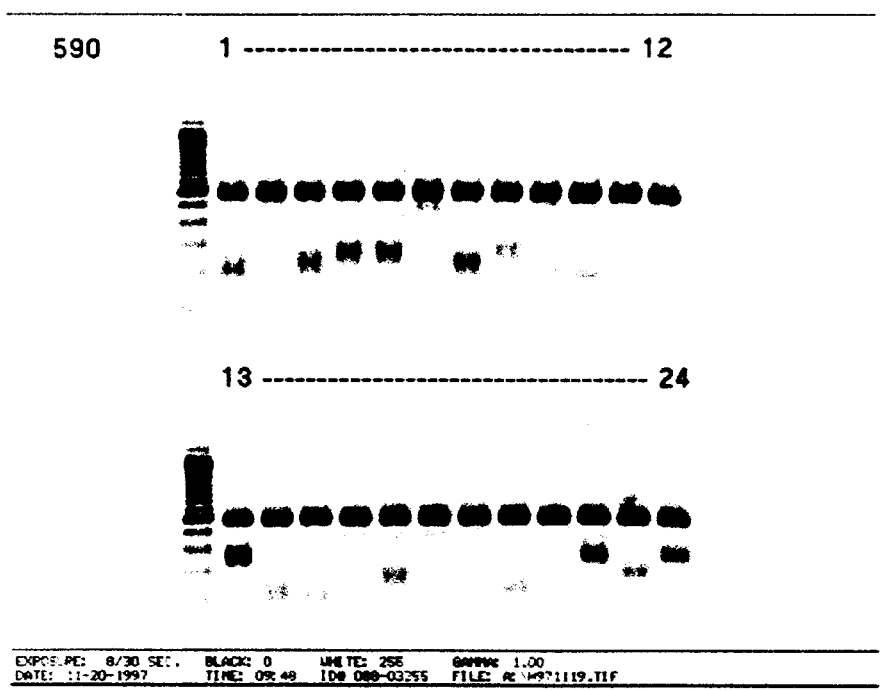
FIG. 12 Polyclonal expansion of CD8+ T cells by CM/P.

Similarly, adult peripheral blood LDMNC were cultured with CM/P for 25 days. This time point represents the CD8-dominant stage (Example 6, FIG. 5). Vβ analysis again revealed the presence of all 24 Vβ genes (FIG. 12). These results indicate that the CD8+ T cells expanded from the LDMNC with CM/P are also polyclonal.

Example 10

Characterization of Expanded T Cells

Figure 13:
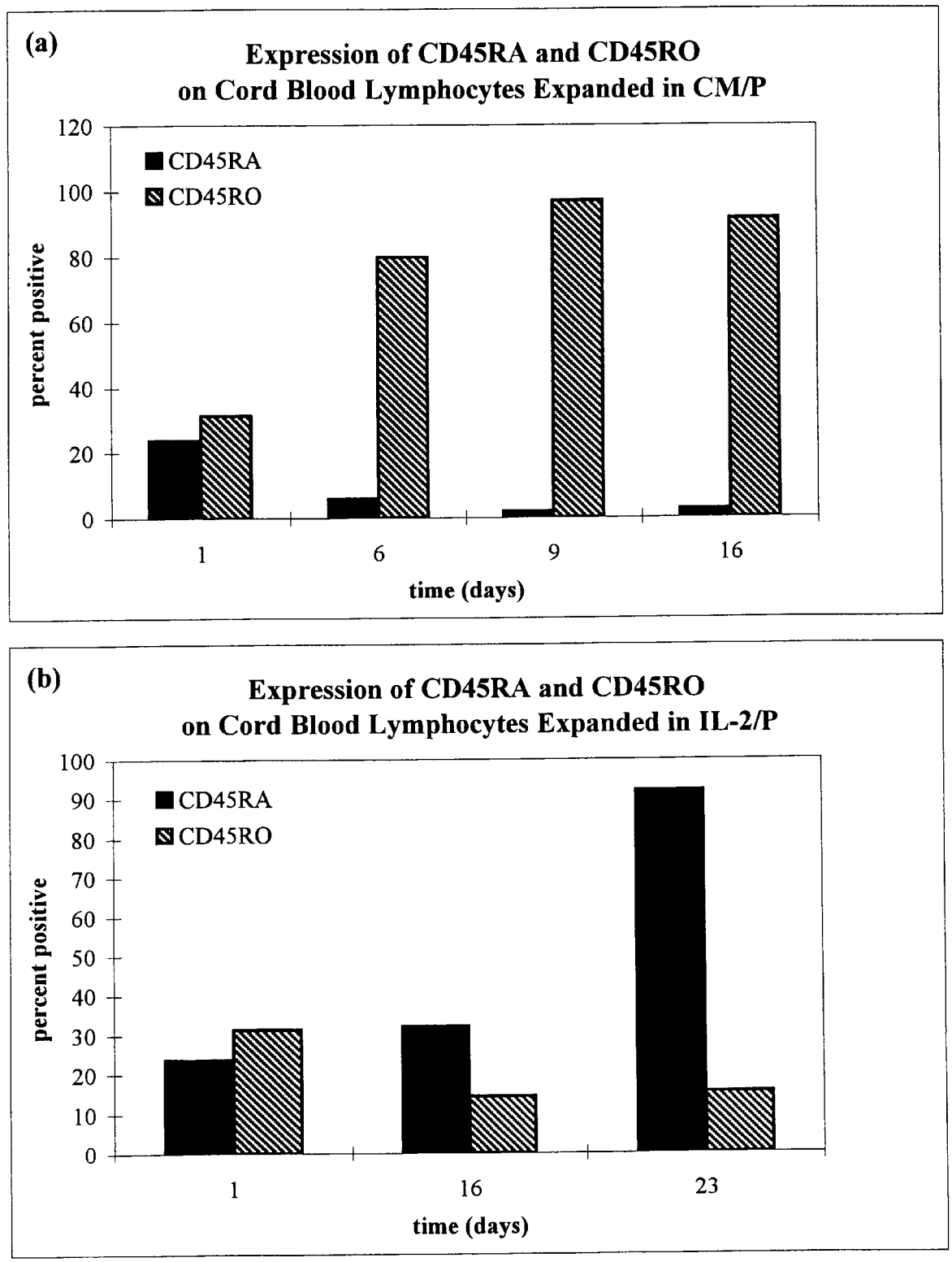
FIG. 13 Expression of CD45RA and CD45RO on cord blood lymphocytes expanded in (*a*) CM/P and (*b*) IL-2/P.

FIG. 13a shows the expression of the CD45 isoforms RA and RO on umbilical cord blood lymphocytes during culture with CM/P. Prior to culture, approximately 24% of the cells express the naive T cell marker CD45RA, while 31% express the memory T cell marker CD45RO. Within 6 days in culture, almost all of the cells (>90%) express the RO isoform, and this phenotype is maintained throughout the culture. By contrast, the majority (>90%) of umbilical cord blood mononuclear cells cultured with IL-2/P express the naive RA phenotype (FIG. 13b).

Figure 14:
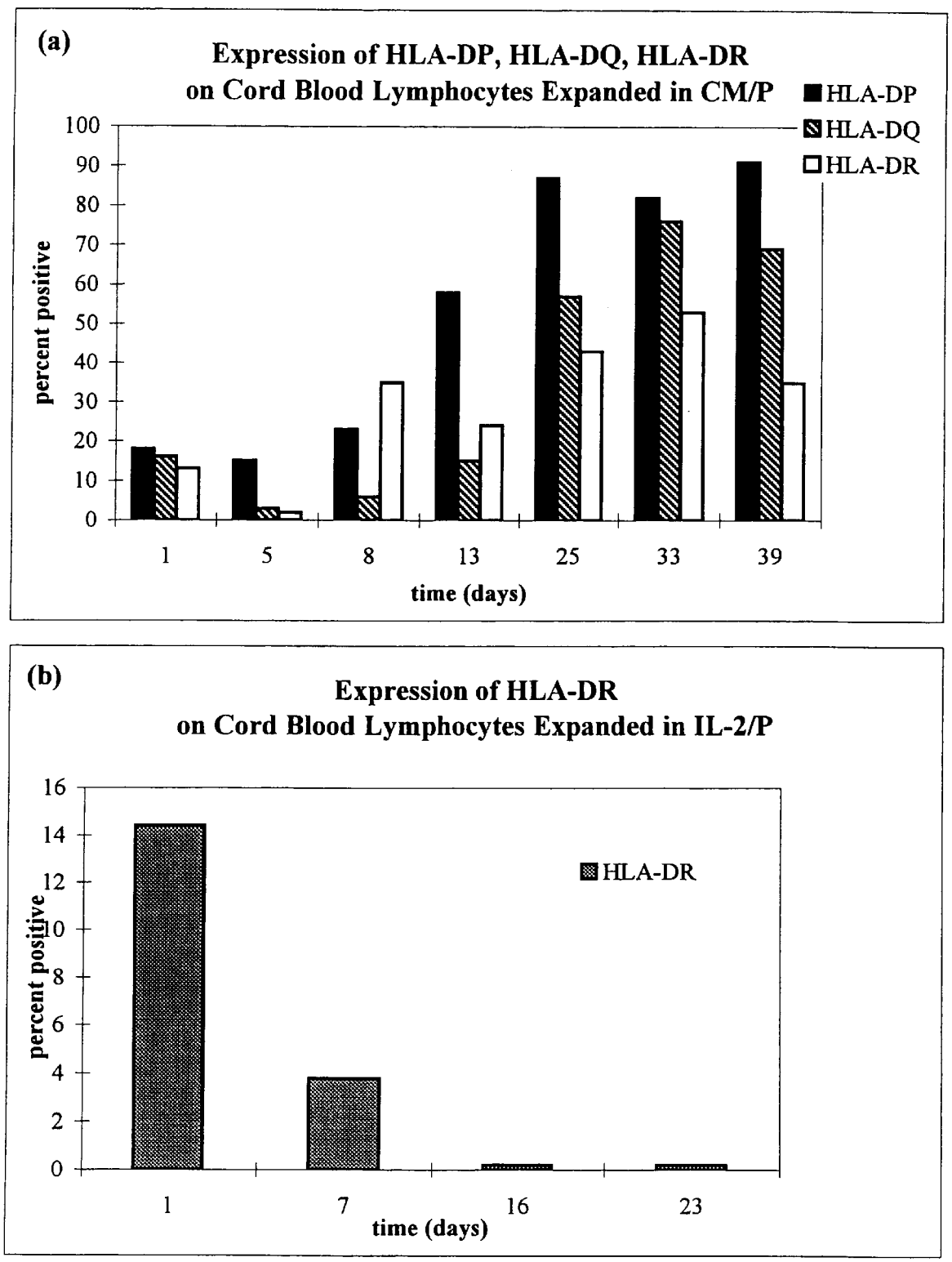
FIG. 14 Expression of (*a*) HLA-DP, HLA-DQ and HLA-DR on cord blood lymphocytes expanded in CM/P and (*b*) HLA-DR on cord blood lymphocytes expanded in IL-2/P.

FIG. 14a shows the expression of the class II major histocompatibility (MHC) antigens, HLA-DP, HLA-DQ and HLA-DR, on umbilical cord blood lymphocytes during culture with CM/P. Expression of class II MHC molecules on T cells is indicative of an enhanced activation state. Thus, these results indicate a progressive increase in the proportion of T cells that become activated during culture with CM/P. By contrast, umbilical cord blood mononuclear cells cultured with IL-2/P do not express HLA-DR (FIG. 14b).

Figure 15:
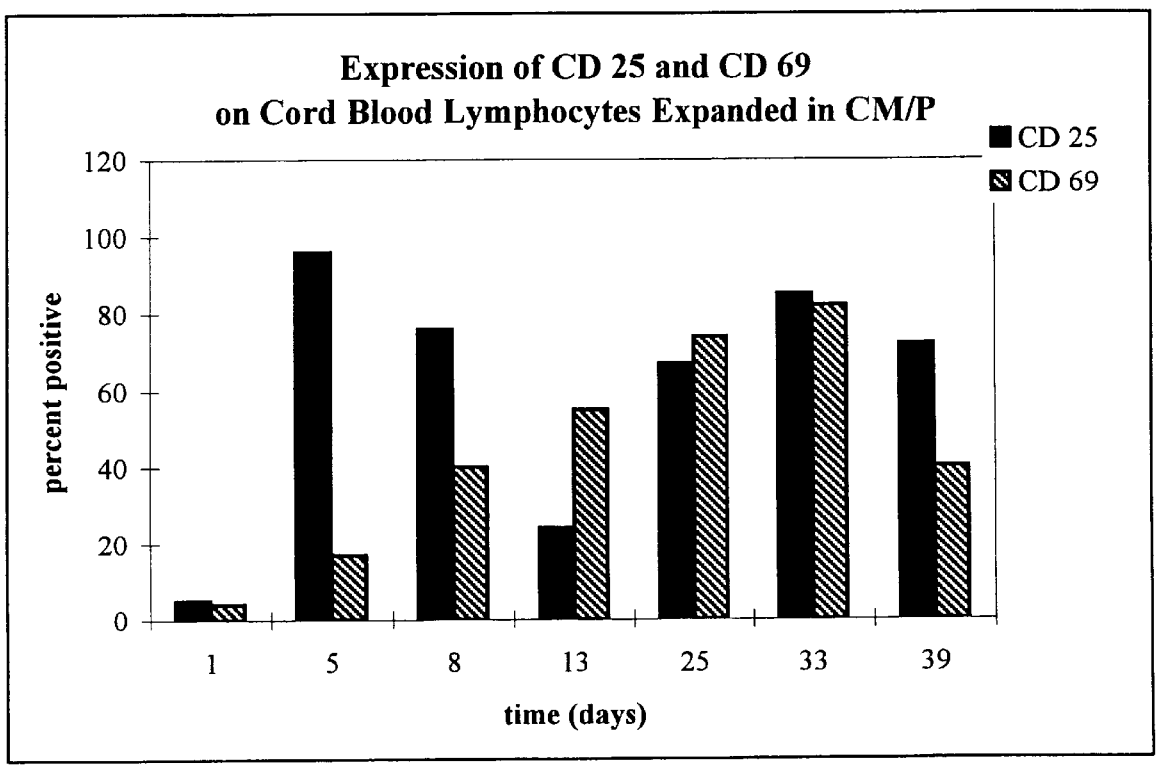
FIG. 15 Expansion of CD25 and CD69 on cord blood lymphocytes expanded in CM/P.

FIG. 15 shows the expression of CD25 and CD69 on umbilical cord blood lymphocytes during culture with CM/P. Neither CD25 nor CD69 are expressed on resting or naive T cells. CD25 is a component polypeptide chain of the high affinity IL-2 receptor (IL-2Rα chain) and its expression on T cells is associated with activation. The proportion of cells expressing CD25 rises quickly at the beginning of the cultures and then decreases during the phase at which the culture switches from a CD4-dominated to a CD8-dominated culture. CD25 expression increases again thereafter. CD69, known as the activation inducer molecule, is also associated with early T cell activation. The proportion of cells expressing CD69 increases more gradually throughout the culture.

Example 11

Expansion of Distinct Lymphocyte Subsets with CM

A. Expansion of NK Cells

Figure 16:
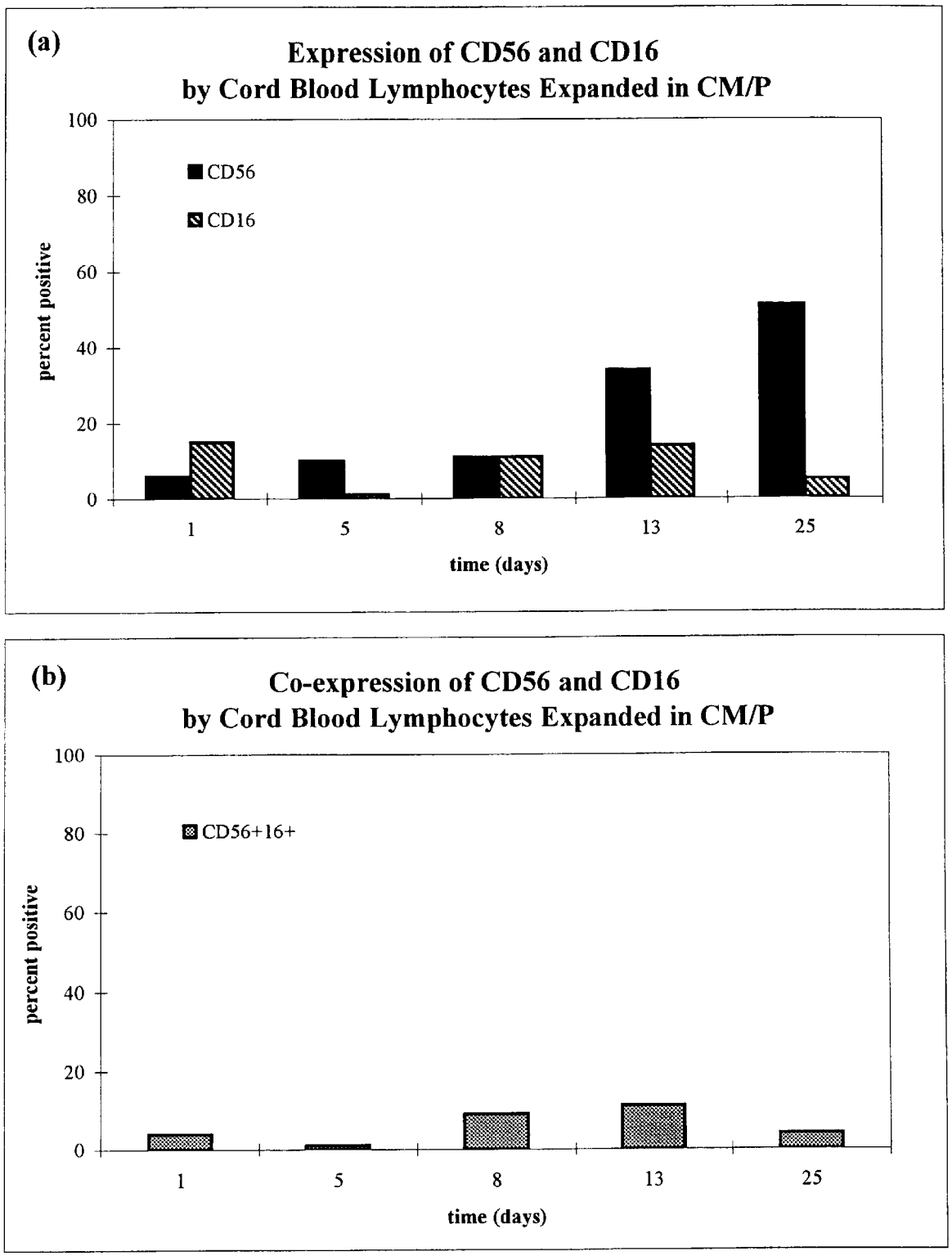
FIG. 16(*a*) Expression and (*b*) co-expression of CD56 and CD16 on cord blood lymphocytes expanded in CM/P.

FIG. 16a shows the expression of CD56 and CD 16 on umbilical cord blood lymphocytes during culture with CM/P. After 8 days, a significant proportion of cells express the NK (natural killer) cell phenotype CD56+/CD16+ (FIG. 16b). Thus, this technique of expanding blood cells with CM is also useful for expanding NK cells.

B. Expansion of CD8+, CD3+, TcRαβ+, CD56+ and CD16- Cells

Figure 17:
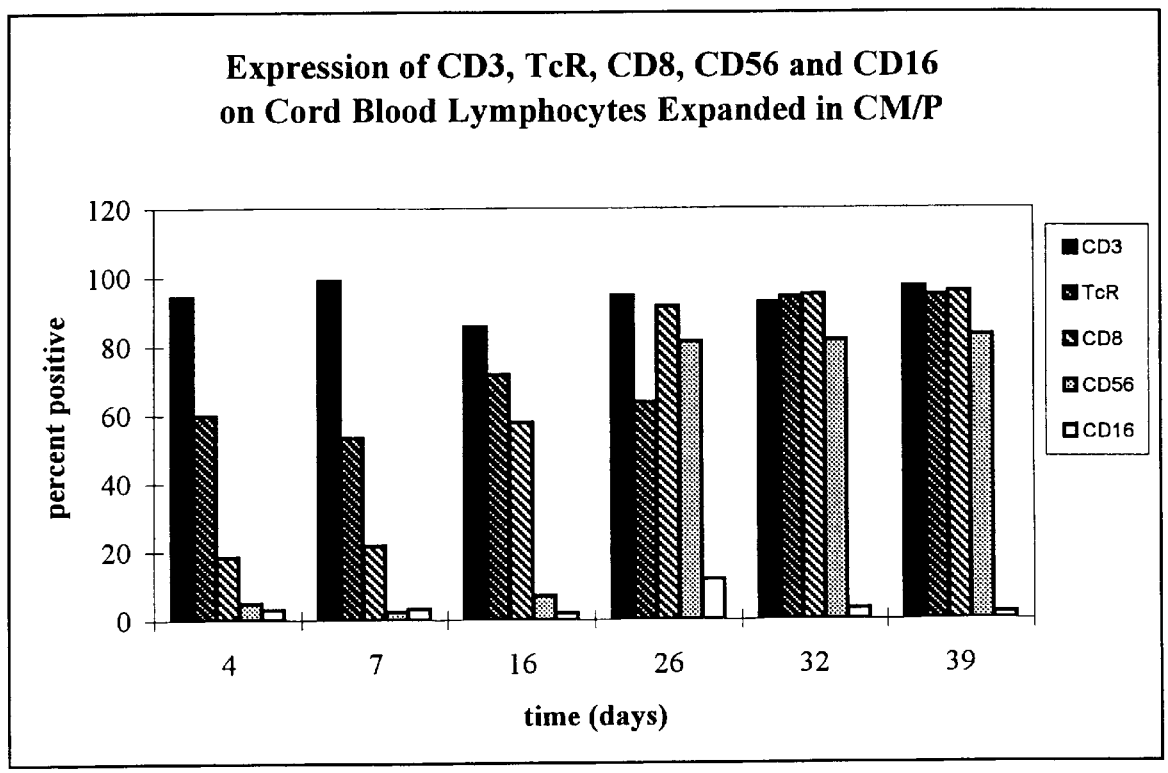
FIG. 17 Expression of CD3, CD8, TcR$\alpha\beta$, CD56 and CD16 on cord blood lymphocytes expanded in CM/P.

FIG. 17 shows the expression of the T cell markers CD3, CD8 and TcRαβ, and the NK cell markers CD56 and CD16, on umbilical cord blood lymphocytes during culture with CM/P. The increase in the proportion of CD8+ T cells during the later stage of the culture is accompanied by an increase in the expression of CD56, but not a concomitant increase in the expression of CD16. Thus, this techniques of expanding blood cells with CM is also useful for expanding a subset of T cells bearing the phenotype CD8+, CD3+, TcRαβ+, CD56+ and CD16-.

C. Expansion of Double-Positive and Double-Negative Cells

Figure 18:
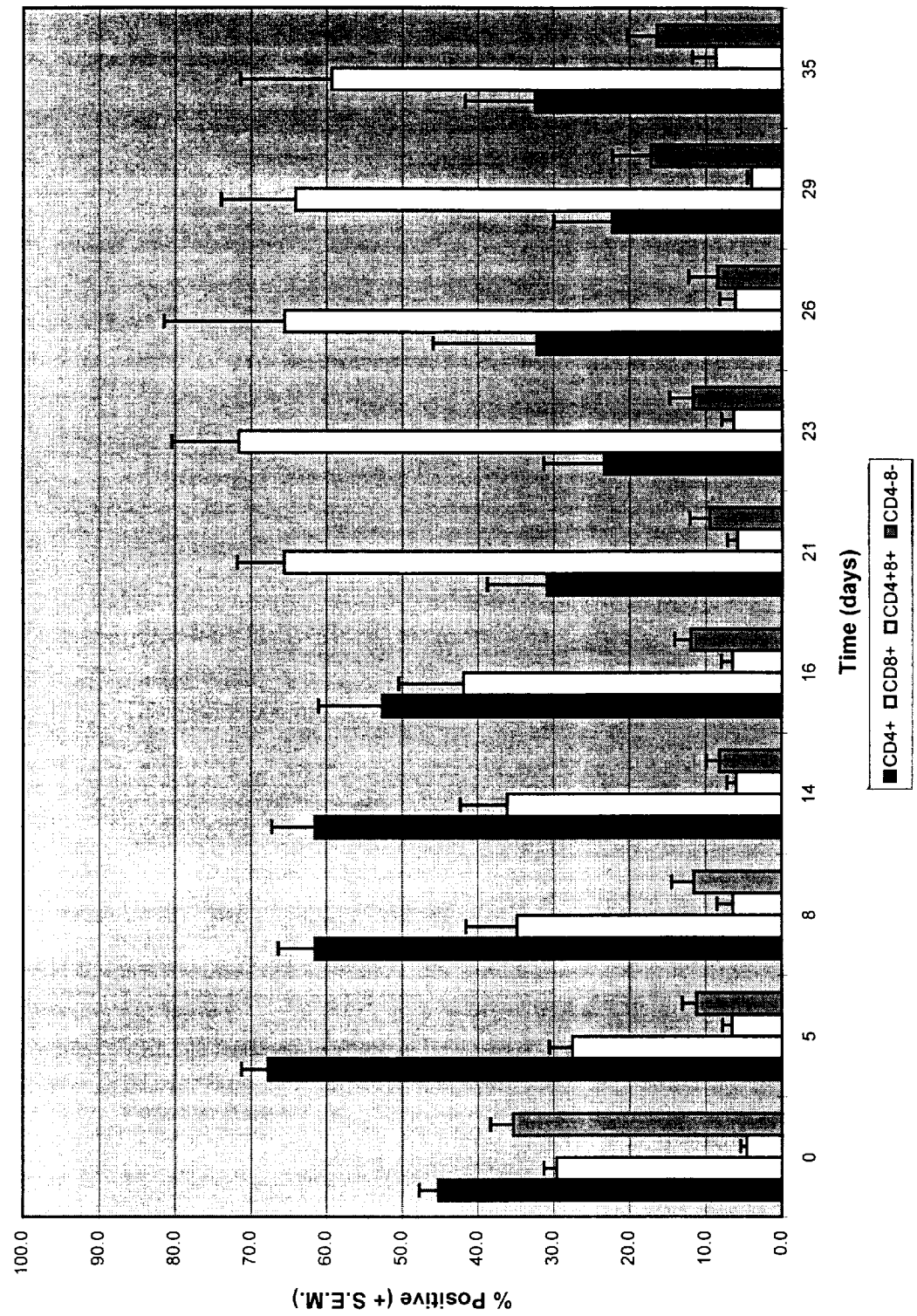
FIG. 18 Average percent of CD4+, CD8+, CD4+/CD8+ and CD4−/CD8− adult blood cells during culture with CM.
Figure 19:
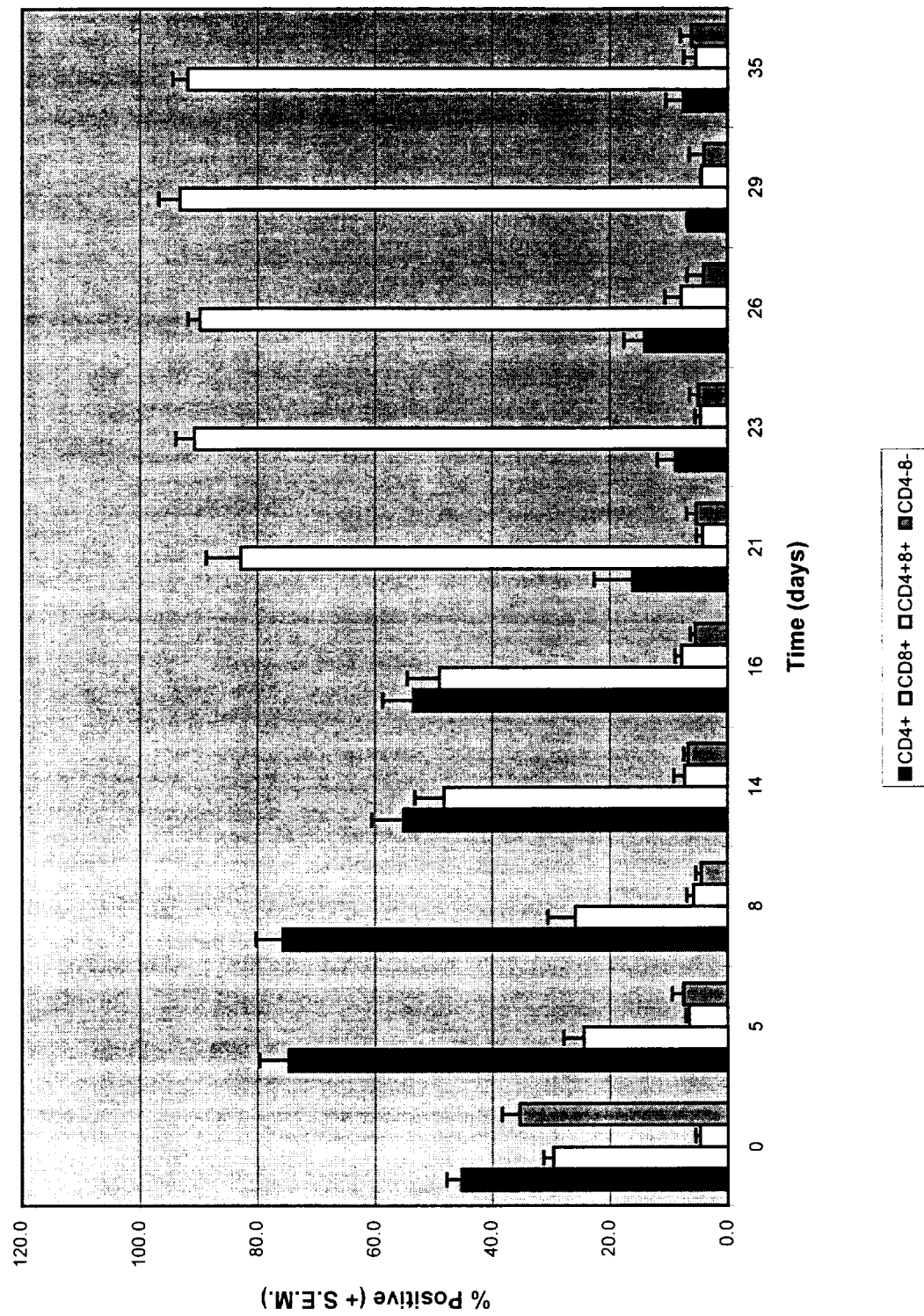
FIG. 19 Average percent of CD4+, CD8+, CD4+/CD8+ and CD4−/CD8− adult blood cells during culture with CM/P.

FIGS. 18 and 19 show the expression of CD4 and CD8 on adult blood LDMNC during culture with CM and CM/P, respectively. As shown in FIG. 18, the percentage of CD4+ cells increased rapidly from 45.2%, maintaining a weighted percentage of 61.9% over days 5 through 16, after which the percentage fell to a weighted average of 27.3% over days 21 through 35. The average percentage of CD8+ cells on fresh LDMNC was 29.6%. The percentage of CD8+ cells was maintained at a weighted average of 34.2% over days 5 through 16, after which the percentage rapidly increased to a weighted average of 65.6% over days 21 through 35. The average percentage of CD4+/CD8+ cells over time was maintained in the range 4.0% to 8.7% indicating growth at a constant rate. The initial percentage of CD4-/CD8- cells was 35.3% which includes non-T cells. The average percentage over days 5 through 26 was maintained in the range 8.4% to 12.0%. Days 29 and 35 had averages of 17.2% and 16.4%, respectively.

As shown in FIG. 19, the percentage of CD4+ cells increased rapidly from 45.2%, maintaining a weighted percentage of 75.2% over days 5 through 8, dropping to a weighted average percentage of 54.7% over days 14 through 16. The average percentage of CD4+ cells fell to a weighted average of 10.7% over days 21 through 35. The percentage of CD8+ cells on fresh LDMNC was 29.6%. The percentage of CD8+ cells was maintained at a weighted average of 25.0% over days 5 and 8, increasing to a weighted average percentage of 48.3% over days 14 and 16. The percentage of CD8+ cells rapidly increased to a weighted average of 89.1% over days 21 through 35. The average percentage of CD4+/CD8+ cells over time was maintained in the range 4.2% to 7.8% indicating growth at a constant rate. The initial percentage of CD4-/CD8- cells was 35.3% which includes non-T cells. The average percentage over days 5 through 35 was maintained in the range 4.0% to 7.5%.

In both cultures, the usual pattern of CD4+ and CD8+ T cell growth was obtained. A significant proportion of T cells throughout both cultures were CD3+ and co-express CD4 and CD8, or lack both CD4 and CD8. These T cells are called double-positive and double-negative T cells, respectively, and are characteristic of immature T cells that are usually present only within the thymus. The maintenance of double-positive and double-negative T cells in the presence of significant overall cell expansion indicates that these immature T cell subsets also proliferate. Thus, the technique of expanding cells with CM is useful for expanding double-positive and double-negative T cells.

Example 12

Expansion of Antigen-specific Mouse T Cells with CM

SJL mice were immunized with 500 μg of guinea pig myelin basic protein (MBP) emulsified in Freund's Complete Adjuvant (FCA). Ten days later, cells obtained from the draining lymph nodes (LNC) of five mice were pooled and incubated at a concentration of 5×10$^6$ cells/ml in the presence of 50 μg/ml MBP antigen for ten days. LNC were washed twice with media and tested for antigen specificity. One×10$^5$ LNC were added to 1×10$^6$ syngeneic, mitomycin C-treated, antigen presenting cells in the presence or absence of 50 μg/ml of MBP antigen. Proliferation was measured 5 days later by $^3$H-thymidine incorporation into DNA. Significant proliferation occurred only when MBP antigen was included (FIG. 20a), indicating the presence of MBP-specific T cells (M-LNC). M-LNC were cultured with 5% CM for 14 days resulting in a 738-fold expansion. At this time, antigen specificity was re-tested as described above. Again, proliferation occurred only in the presence of MBP (FIG. 20b). These results indicate that antigen specific T cells can be expanded with CM and that the expanded cells maintain their antigen specificity.

Other embodiments and uses of the invention will be apparent to those skilled in the art from consideration of the specification and practice of the invention disclosed herein. All U.S. patents and patent applications, including provisional application Ser. No. 60/037,245, and all other documents referenced herein, for whatever reason, are specifically incorporated by reference. It is intended that the specification and examples be considered exemplary only, with the true scope and spirit of the invention being indicated by the following claims.

We claim:

1. A process for increasing the ratio of CD8:CD4-T-cells in culture which comprises adding an effective amount of umbilical cord plasma to a suitable T-cell culture medium to obtain a resultant medium, and culturing appropriate T-cells or their precursors in the resultant medium for an effective period of time.

2. The process of claim 1 where the plasma is human umbilical cord plasma.

3. The process of claim 1 wherein the plasma comprises between 2% and 10% of the total culture volume.

4. A process for increasing the ratio of TcRγδ: TcRαβ cells in culture which comprises adding an effective amount of umbilical cord plasma to a suitable T-cell culture medium to obtain a resultant medium, and culturing appropriate T-cells or their precursors in the resultant medium for an effective period of time.

5. The process of claim 4 where the plasma is human umbilical cord plasma.

6. The process of claim 4 wherein the plasma comprises between 2% and 10% of the total culture volume.

* * * * *